US012673106B2

(12) United States Patent
Zhang et al.

(10) Patent No.: US 12,673,106 B2
(45) Date of Patent: Jul. 7, 2026

(54) MODULATORS OF NUCLEAR RECEPTOR SUBFAMILY 4 GROUP A MEMBER 1 (NR4A1) AND USES THEREOF

(71) Applicant: University of Florida Research Foundation, Incorporated, Gainesville, FL (US)

(72) Inventors: Weizhou Zhang, Gainesville, FL (US); Guangrong Zheng, Gainesville, FL (US); Daohong Zhou, Gainesville, FL (US); Yufeng Xiao, Gainesville, FL (US); Lei Wang, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 675 days.

(21) Appl. No.: 18/023,696

(22) PCT Filed: Aug. 27, 2021

(86) PCT No.: PCT/US2021/048007

§ 371 (c)(1),
(2) Date: Feb. 27, 2023

(87) PCT Pub. No.: WO2022/072094

PCT Pub. Date: Apr. 7, 2022

(65) Prior Publication Data

US 2023/0330237 A1 Oct. 19, 2023

Related U.S. Application Data

(60) Provisional application No. 63/071,733, filed on Aug. 28, 2020.

(51) Int. Cl.

| | |
|---|---|
| ***A61K 47/55*** | (2017.01) |
| ***A61K 45/06*** | (2006.01) |
| ***A61P 35/00*** | (2006.01) |
| ***C07D 401/04*** | (2006.01) |
| ***C07K 5/062*** | (2006.01) |

(52) U.S. Cl.

CPC .............. *A61K 47/55* (2017.08); *A61K 45/06* (2013.01); *A61P 35/00* (2018.01)

(58) Field of Classification Search

CPC .......................... C07K 5/06043; C07D 401/04

See application file for complete search history.

(56) References Cited

U.S. PATENT DOCUMENTS

| | | | |
|---|---|---|---|
| 2013/0108602 | A1 | 5/2013 | Hedrick et al. |
| 2018/0362575 | A1 | 12/2018 | Mazitschek et al. |

FOREIGN PATENT DOCUMENTS

| | | | |
|---|---|---|---|
| WO | WO 2018/006804 A1 | 1/2018 | |
| WO | WO 2020/163823 A2 | 8/2020 | |

OTHER PUBLICATIONS

Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022).*

Cecil Textbook of Medicine, 20th Ed, vol. 1, 1997, p. 1004-1010 (Year: 1997).*

Klaić L, Morimoto RI, Silverman RB. Celastrol analogues as inducers of the heat shock response. Design and synthesis of affinity probes for the identification of protein targets. ACS Chem Biol. May 18, 2012;7(5):928-37. doi: 10.1021/cb200539u. Epub Mar. 14, 2012. PMID: 22380712; PMCID: PMC3356480. (Year: 2012).*

Invitation to Pay Additional Fees for Application No. PCT/US2021/048007, mailed Apr. 14, 2022.

International Search Report and Written Opinion for Application No. PCT/US2021/048007, mailed Jun. 6, 2022.

International Preliminary Report on Patentability (Chapter I) for Application No. PCT/US2021/048007, mailed Mar. 9, 2023.

Hu et al., Celastrol-Induced Nur77 Interaction with TRAF2 Alleviates Inflammation by Promoting Mitochondrial Ubiquitination and Autophagy. Mol Cell. Apr. 6, 2017;66(1):141-153.e6. doi: 10.1016/j.molcel.2017.03.008.

Chen et al., NR4A transcription factors limit CAR T cell function in solid tumours. Nature. Mar. 2019;567(7749):530-534. doi: 10.1038/s41586-019-0985-x. Epub Feb. 27, 2019. Author manuscript, 42 pages.

Chen et al., SAR study of celastrol analogs targeting Nur77-mediated inflammatory pathway. Eur J Med Chem. Sep. 1, 2019;177:171-187. doi: 10.1016/j.ejmech.2019.05.009. Epub May 12, 2019.

Deutsch et al., NR4A1-mediated apoptosis suppresses lymphomagenesis and is associated with a favorable cancer-specific survival in patients with aggressive B-cell lymphomas. Blood. Apr. 10, 2014;123(15):2367-77. doi: 10.1182/blood-2013-08-518878. Epub Feb. 19, 2014.

Fassett et al., Nuclear receptor Nr4a1 modulates both regulatory T-cell (Treg) differentiation and clonal deletion. Proc Natl Acad Sci U S A. Mar. 6, 2012;109(10):3891-6. doi: 10.1073/pnas.1200090109. Epub Feb. 15, 2012.

Hedrick et al., NR4A1 Antagonists Inhibit β1-Integrin-Dependent Breast Cancer Cell Migration. Mol Cell Biol. Apr. 15, 2016;36(9):1383-94. doi: 10.1128/MCB.00912-15. Erratum in: Mol Cell Biol. Aug. 28, 2017;37(18):e00197-17. doi: 10.1128/MCB.00197-17.

Hedrick et al., Nuclear Receptor 4A1 (NR4A1) as a Drug Target for Renal Cell Adenocarcinoma. PLoS One. Jun. 2, 2015;10(6):e0128308. doi: 10.1371/journal.pone.0128308.

Hedrick et al., Nuclear receptor 4A1 as a drug target for breast cancer chemotherapy. Endocr Relat Cancer. Oct. 2015;22(5):831-40. doi: 10.1530/ERC-15-0063. Epub Jul. 30, 2015.

(Continued)

*Primary Examiner* — Bruck Kifle
*Assistant Examiner* — Kevin S Martin
(74) *Attorney, Agent, or Firm* — Wolf, Greenfield & Sacks, P.C.

(57) ABSTRACT

Modulators of Nuclear Receptor Subfamily 4 Group A Member 1 (NR4A1) are described as well as their use as therapeutic agents for disease, disorders, or symptoms thereof, including those where modulation of NR4A1 is implicated. Such disease and disorders include cancer.

19 Claims, 16 Drawing Sheets

(56) References Cited

OTHER PUBLICATIONS

Hedrick et al., Potent inhibition of breast cancer by bis-indole-derived nuclear receptor 4A1 (NR4A1) antagonists. Breast Cancer Res Treat. Aug. 2019;177(1):29-40. doi: 10.1007/s10549-019-05279-9. Epub May 22, 2019. Author manuscript, 18 pages.
Hedrick et al., TGFβ-Induced Lung Cancer Cell Migration Is NR4A1-Dependent. Mol Cancer Res. Dec. 2018;16(12):1991-2002. doi: 10.1158/1541-7786.MCR-18-0366. Epub Aug. 2, 2018.
Hedrick et al., Transforming Growth Factor β/NR4A1-Inducible Breast Cancer Cell Migration and Epithelial-to-Mesenchymal Transition Is p38α (Mitogen-Activated Protein Kinase 14) Dependent. Mol Cell Biol. Aug. 28, 2017;37(18):e00306-17. doi: 10.1128/MCB.00306-17.
Hibino et al., Inhibition of Nr4a Receptors Enhances Antitumor Immunity by Breaking Treg-Mediated Immune Tolerance. Cancer Res. Jun. 1, 2018;78(11):3027-3040. doi: 10.1158/0008-5472.CAN-17-3102. Epub Mar. 20, 2018.
Karki et al., A Bis-Indole-Derived NR4A1 Antagonist Induces PD-L1 Degradation and Enhances Antitumor Immunity. Cancer Res. Mar. 1, 2020;80(5):1011-1023. doi: 10.1158/0008-5472.CAN-19-2314. Epub Jan. 7, 2020.
Khan et al., A selective BCL-XL PROTAC degrader achieves safe and potent antitumor activity. Nat Med. Dec. 2019;25(12):1938-1947. doi: 10.1038/s41591-019-0668-z. Epub Dec. 2, 2019. Author manuscript, 52 pages.
Kolb et al., Obesity-associated inflammation promotes angiogenesis and breast cancer via angiopoietin-like 4. Oncogene. Mar. 2019;38(13):2351-2363. doi: 10.1038/s41388-018-0592-6. Epub Dec. 5, 2018. Author manuscript, 24 pages.
Kolb et al., Obesity-associated NLRC4 inflammasome activation drives breast cancer progression. Nat Commun. Oct. 6, 2016;7:13007. doi: 10.1038/ncomms13007.
Li et al., Nuclear Receptor Nur77 Facilitates Melanoma Cell Survival under Metabolic Stress by Protecting Fatty Acid Oxidation. Mol Cell. Feb. 1, 2018;69(3):480-492.e7. doi: 10.1016/j.molcel.2018.01.001. Epub Jan. 27, 2018.
Liu et al., A unique pharmacophore for activation of the nuclear orphan receptor Nur77 in vivo and in vitro. Cancer Res. May 1, 2010;70(9):3628-37. doi: 10.1158/0008-5472.CAN-09-3160. Epub Apr. 13, 2010.
Liu et al., Apoptotic signals delivered through the T-cell receptor of a T-cell hybrid require the immediate-early gene nur77. Nature. Jan. 20, 1994;367(6460):281-4. doi: 10.1038/367281a0.
Liu et al., Genome-wide analysis identifies NR4A1 as a key mediator of T cell dysfunction. Nature. Mar. 2019;567(7749):525-529. doi: 10.1038/s41586-019-0979-8. Epub Feb. 27, 2019. Author manuscript, 32 pages.
Milbrandt, Nerve growth factor induces a gene homologous to the glucocorticoid receptor gene. Neuron. May 1988;1(3):183-8. doi: 10.1016/0896-6273(88)90138-9.
Mohankumar et al., Nuclear receptor 4A1 (NR4A1) antagonists induce ROS-dependent inhibition of mTOR signaling in endometrial cancer. Gynecol Oncol. Jul. 2019;154(1):218-227. doi: 10.1016/j.ygyno.2019.04.678. Epub Apr. 30, 2019. Author manuscript, 19 pages.
Mullican et al., Abrogation of nuclear receptors Nr4a3 and Nr4a1 leads to development of acute myeloid leukemia. Nat Med. Jun. 2007;13(6):730-5. doi: 10.1038/nm1579. Epub May 21, 2007.
Muscat et al., Research resource: nuclear receptors as transcriptome: discriminant and prognostic value in breast cancer. Mol Endocrinol. Feb. 2013;27(2):350-65. doi: 10.1210/me.2012-1265. Epub Jan. 4, 2013. Erratum. Mol Endocrinol. Oct. 2013;27(10):1790. doi: 10.1210/me.2013-1250.
Narayan et al., FDA Approval Summary: Atezolizumab Plus Paclitaxel Protein-bound for the Treatment of Patients with Advanced or Metastatic TNBC Whose Tumors Express PD-L1. Clin Cancer Res. May 15, 2020;26(10):2284-2289. doi: 10.1158/1078-0432.CCR-19-3545. Epub Jan. 30, 2020.
Neklesa et al., Targeted protein degradation by PROTACs. Pharmacol Ther. Jun. 2017;174:138-144. doi: 10.1016/j.pharmthera.2017.02.027. Epub Feb. 14, 2017.
Schapira et al., Targeted protein degradation: expanding the toolbox. Nat Rev Drug Discov. Dec. 2019;18(12):949-963. doi: 10.1038/s41573-019-0047-y. Epub Oct. 30, 2019.
Sekiya et al., Nr4a Receptors Regulate Development and Death of Labile Treg Precursors to Prevent Generation of Pathogenic Self-Reactive Cells. Cell Rep. Aug. 7, 2018;24(6):1627-1638.e6. doi: 10.1016/j.celrep.2018.07.008.
Wenzl et al., The nuclear orphan receptor NR4A1 and NR4A3 as tumor suppressors in hematologic neoplasms. Curr Drug Targets. 2015;16(1):38-46. doi: 10.2174/1389450115666141120112818.
Woronicz et al., Requirement for the orphan steroid receptor Nur77 in apoptosis of T-cell hybridomas. Nature. Jan. 20, 1994;367(6460):277-81. doi: 10.1038/367277a0.
Wu et al., Characteristics of Nur77 and its ligands as potential anticancer compounds (Review). Mol Med Rep. Dec. 2018;18(6):4793-4801. doi: 10.3892/mmr.2018.9515. Epub Sep. 27, 2018.
Zhan et al., Cytosporone B is an agonist for nuclear orphan receptor Nur77. Nat Chem Biol. Sep. 2008;4(9):548-56. doi: 10.1038/nchembio.106.
Zhou et al., Nuclear receptor NR4A1 promotes breast cancer invasion and metastasis by activating TGF-β signalling. Nat Commun. Mar. 3, 2014;5:3388. doi: 10.1038/ncomms4388.

* cited by examiner

Celastrol:
Kd = 0.26 μM

NR-V03

NR-V07

NR-V04

NR-V46

NR-V50

NR-C58

NR-C91

NR-C92

NR-C93

IV administration 2mg/kg

| Animal | No. of pts used for $t_{1/2}$ | $t_{1/2}$(hr) | $C_0$ (ng/mL) | $AUC_{last}$ (hr*ng/mL) | $AUC_{Inf}$ (hr*ng/mL) | $AUC_{Extr}$(%) | $V_z$ (L/kg) | $V_{ss}$ (L/kg) | CL (mL/min/kg) | $MRT_{Inf}$(hr) | Last time point for $AUC_{last}$(hr) | Time points for $t_{1/2}$(hr) | Rsq |
|---|---|---|---|---|---|---|---|---|---|---|---|---|---|
| Mouse #1 | 3 | 5.46 | 15584 | 2814 | 2844 | 1.06 | 5.54 | 1.24 | 11.7 | 1.76 | 24 | 4, 8, 24 | 0.988 |
| Mouse #2 | 3 | 5.41 | 32378 | 3959 | 3999 | 0.995 | 3.90 | 0.803 | 8.34 | 1.61 | 24 | 4, 8, 24 | 0.976 |
| Mouse #3 | 3 | 5.20 | 18727 | 3596 | 3634 | 1.06 | 4.13 | 1.10 | 9.17 | 1.99 | 24 | 4, 8, 24 | 0.995 |
| N | 3 | 3 | 3 | 3 | 3 | 3 | 3 | 3 | 3 | 3 | | | |
| **Mean** | | **5.36** | **22230** | **3456** | **3492** | **1.04** | **4.52** | **1.05** | **9.74** | **1.79** | | | |
| SD | | 0.14 | 8928 | 585 | 590 | 0.04 | 0.89 | 0.22 | 1.76 | 0.19 | | | |
| CV% | | 2.6 | 40.2 | 16.9 | 16.9 | 3.8 | 19.7 | 21.3 | 18.1 | 10.9 | | | |

FIG. 17A

IP administration 20mg/kg

| Animal | No. of pts used for $t_{1/2}$ | $t_{1/2}$(hr) | $t_{max}$(hr) | $C_{max}$ (ng/mL) | $AUC_{last}$ (hr*ng/mL) | $AUC_{Inf}$ (hr*ng/mL) | $AUC_{Extr}$ (%) | $MRT_{Inf}$ (hr) | $AUC_{Inf}/D$ (hr*kg*ng/mL/mg) | F(%) | Last time point for $AUC_{last}$(hr) | Time points for $t_{1/2}$(hr) | Rsq |
|---|---|---|---|---|---|---|---|---|---|---|---|---|---|
| Mouse #4 | 3 | 8.04 | 2.00 | 3340 | 30530 | 34962 | 12.7 | 10.6 | 1748 | 100 | 24 | 4, 8, 24 | 0.976 |
| Mouse #5 | 3 | 8.42 | 0.500 | 3070 | 29852 | 34781 | 14.2 | 11.2 | 1739 | 99.6 | 24 | 4, 8, 24 | 0.951 |
| Mouse #6 | 3 | 9.28 | 1.00 | 2920 | 27060 | 32911 | 17.8 | 13.1 | 1646 | 94.2 | 24 | 4, 8, 24 | 0.979 |
| N | 3 | 3 | 3 | 3 | 3 | 3 | 3 | 3 | 3 | 3 | | | |
| **Mean** | | **8.58** | **1.17** | **3110** | **29147** | **34218** | **14.9** | **11.7** | **1711** | **98.0** | | | |
| SD | | 0.64 | 0.76 | 213 | 1839 | 1136 | 2.6 | 1.3 | 57 | 3.3 | | | |
| CV% | | 7.4 | 65.5 | 6.8 | 6.3 | 3.3 | 17.6 | 11.3 | 3.3 | 3.3 | | | |

F was based on the calculation of $AUC_{inf}$.

FIG. 17B

MODULATORS OF NUCLEAR RECEPTOR SUBFAMILY 4 GROUP A MEMBER 1 (NR4A1) AND USES THEREOF

CROSS REFERENCE TO RELATED APPLICATIONS

This application is a national stage filing of International PCT Application No. PCT/US2021/048007, filed Aug. 27, 2021, which claims priority to U.S. Provisional Application No. 63/071,733, filed Aug. 28, 2020, the contents of each of which are incorporated herein by reference in their entirety.

GOVERNMENT SUPPORT INFORMATION

This invention was made with government support under Grant Numbers W81XWH-21-1-0004 and W81XWH-21-1-0005, awarded by the Defense Health Agency, Medical Research and Development Branch. The government has certain rights in the invention.

REFERENCE TO A JOINT RESEARCH AGREEMENT

This invention was made in whole or in part from funding received under contract AGR DTD 12-1-20 received from Sanofi.

BACKGROUND

Current drug development mainly focuses on one molecular target in one certain cell type. For example, most targeted therapeutics focus on inhibiting cancer cell intrinsic signaling and most immunotherapies focus on activating CD8+ T cells, such as immune checkpoint inhibitors (ICI). The question remains whether it is possible to purposely inhibit one molecule/pathway to inhibit cancer cells at the same time eliciting anti-cancer immunity. Recent efforts have focused on exploring targetable molecules that play critical roles in both cancer cells as well as immune suppressive cell types including Tregs and exhausted T cells. Several molecular targets were identified, including Nuclear Receptor Subfamily 4 Group A Member 1 (NR4A1, also named as NUR77, NAK-1, NGFIB, etc.). Although NR4A1 has been shown to be a tumor suppressor in acute myeloid lymphomas (1, 2) with its loss associated with aggressive B-cell lymphomas (3), most literature supports the role of NR4A1 in cancer progression either by directly promoting cancer growth/invasion/metastasis (4-7) or via promoting an immune-permissive tumor microenvironment (TME) (8-10).

A first systematic study of nuclear receptor in breast cancer identified that NR4A1 is one of the most upregulated nuclear receptors in breast cancer relative to normal breast tissues (11). Further reports strongly support the critical role of NR4A1 in the selective activation of TGFβ signaling transduction in breast cancer, consequently contributing to epithelial-mesenchymal transition, invasion, and metastasis (12) in a p38α-MAP kinase dependent manner (6). Small molecule inhibitors have been attempted to antagonize NR4A1 in breast cancer cells in experimental settings (4-7) that showed inhibitory effects on NR4A1 activity and inhibited cancer cell proliferation and invasion. Similar results were shown in other cancer types as well, including renal clear cell carcinomas (13), endometrial cancers (14), melanoma (15), etc.

NR4A1 was known as an immediate response gene that can be induced by various stimuli (16, 17) including T cell-receptor (TCR)-mediated signaling transduction (18, 19); the latter induces an apoptotic cell death of T cells, a process that is important for negative selection for clonal deletion of self-reactive T cells (18, 19). NR4A1 is also critical for Treg development by inducing FoxP3 expression and lineage commitment (20). Interestingly, under the context of cancer therapy, NR4A1 and its closely related members NR4A2 and NR4A3 are highly elevated in exhausted T cells; depletion of NR4A family members is important to rejuvenate cancer specific CD8 T cells (8, 9). Preliminary data clearly showed dramatic elevated NR4A1 mRNA levels in TI-Tregs related to blood Tregs. Deletion of NR4A1 family members in mice led to protective anti-tumor immunity in mouse model of cancers (21). It is expected that NR4A1 is important for inducing CD8 T cell dysfunction and accumulation of TI-Tregs, two critical immune regulations that render cancer evasion of immune surveillance.

PROTACs are bivalent small molecules, one pharmacophore binding to target protein and the other pharmacophore recruiting an E3 ligase. These bivalent molecules can bring the target (NR4A1) to the vicinity of the E3 ligase (FIG. 1, VHL or CRBN) for polyubiquitination and subsequent proteasome degradation (23, 24). PROTACs act catalytically to induce protein degradation in a sub-stoichiometric manner and their effect is not limited by equilibrium occupancy. Therefore, PROTACs often have a better and longer-acting activity than traditional occupancy-driven protein inhibitors. In addition, PROTACs induce specific protein degradation by recruiting target protein to an E3 ligase, which is based on the recognition of target protein by the 'warhead' of PROTACs. As such, the warhead does not need to function as an inhibitor. The ligands (both antagonists and agonists) of NR4A1 were recently reviewed and most with submicromolar dissociation constants (Kd) (25). Although the known NR4A1 ligands do not have sufficient potency for clinical translation, they could be used for the construction of PROTACs that can potently induce NR4A1 degradation. Thus, there is a need in the art to design and synthesize PROTAC NR4A1 degraders (NR4A1-Ps) that can simultaneously target breast cancer cells, Tregs, and exhausted CD8 T cells for efficient tumor elimination.

BRIEF SUMMARY OF THE INVENTION

Provided herein are compounds (e.g., Formula (I)), their mechanism of action, and methods of treating cancer using the compounds described herein (e.g., Formula (I)). In another aspect, the cancer is breast cancer, lung cancer, liver cancer, pancreatic cancer, intestinal cancer, cancer of the spleen, colon cancer, melanoma, thyroid carcinoma, esophageal adenocarcinomas, or bladder cancer. In some embodiments, the cancer is breast cancer, lung cancer, or melanoma.

In another aspect, provided herein is a compound of the formula:

NR-V03
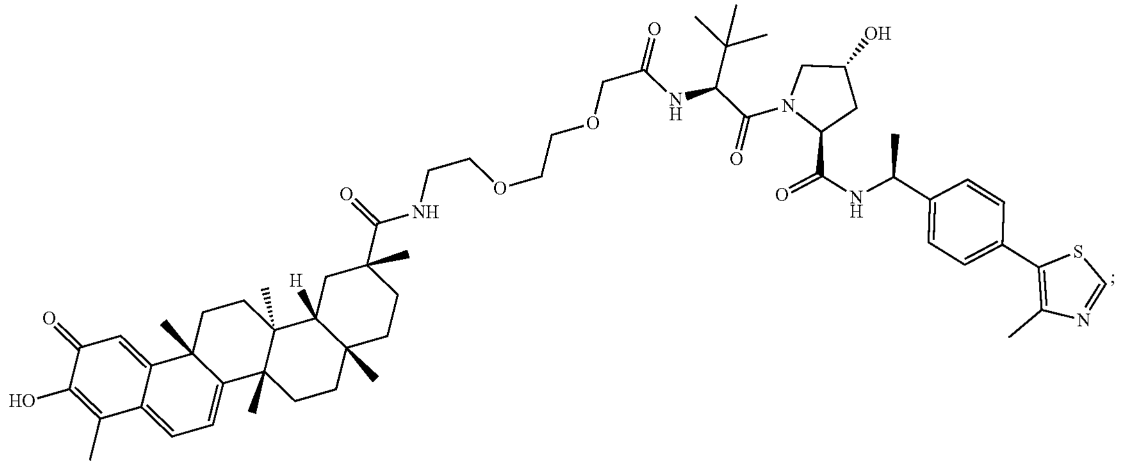
NR-V07
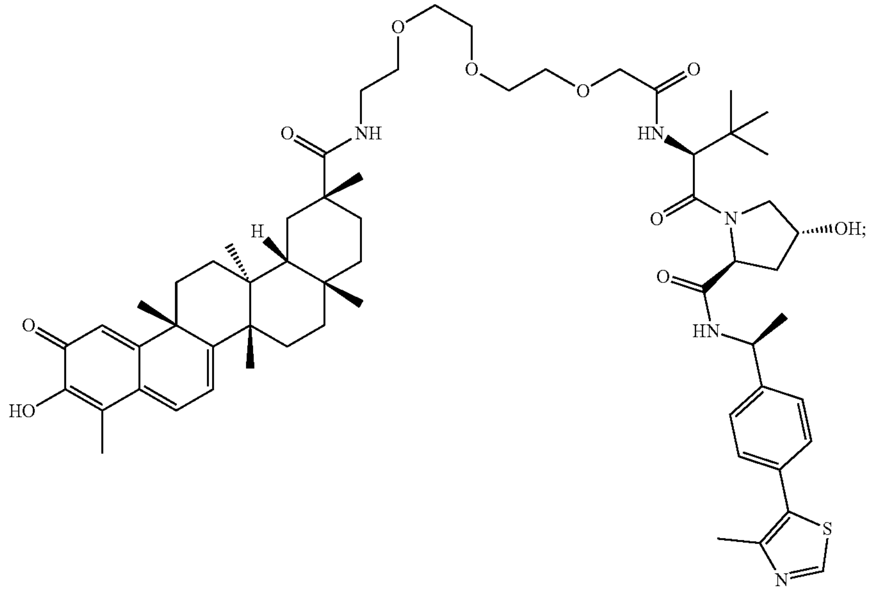
NR-V04
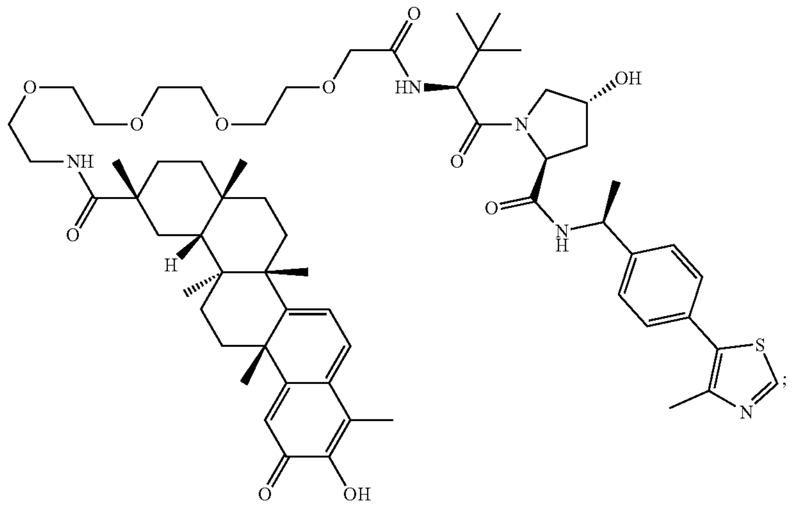

-continued
NR-V46
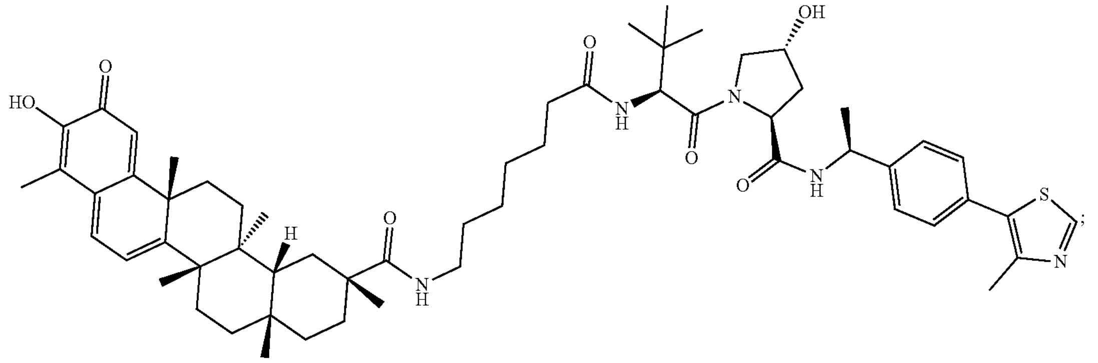
NR-V50
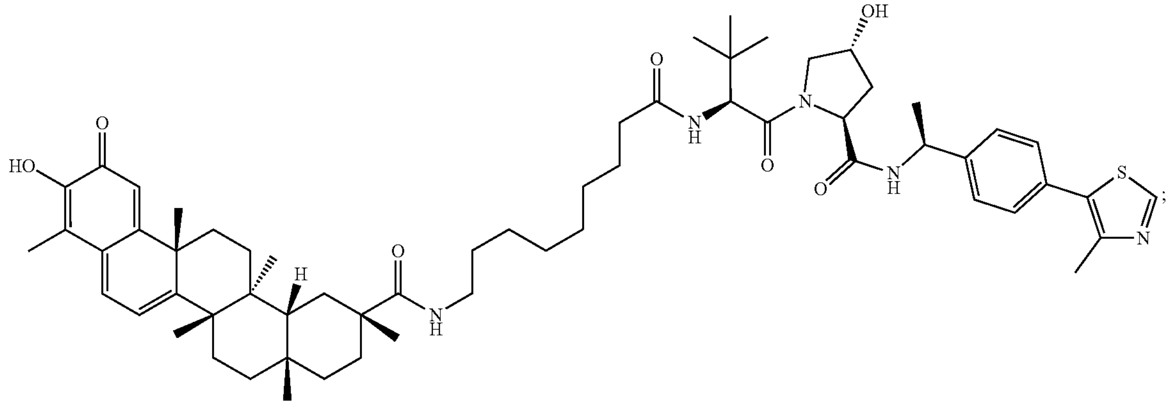
NR-C58
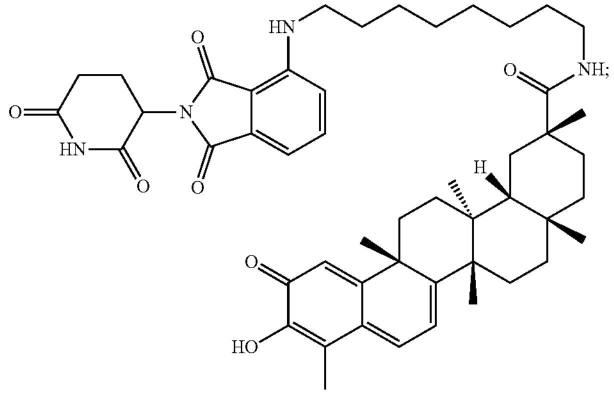
NR-C91
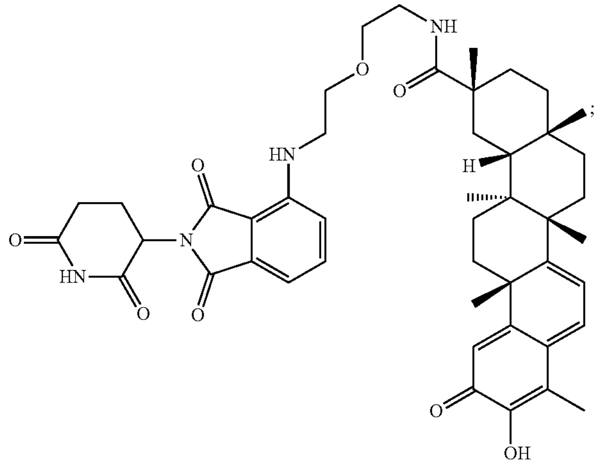

-continued
NR-C92
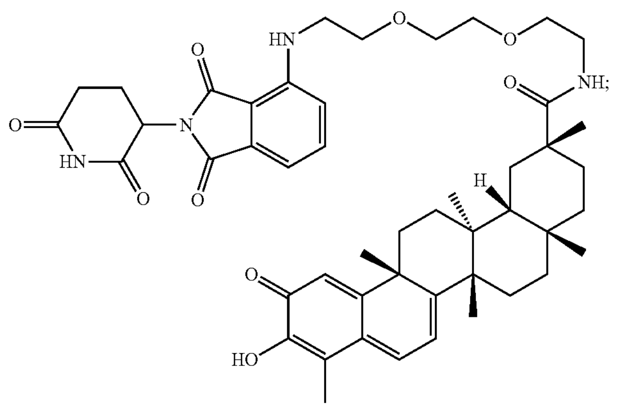
NR-C93
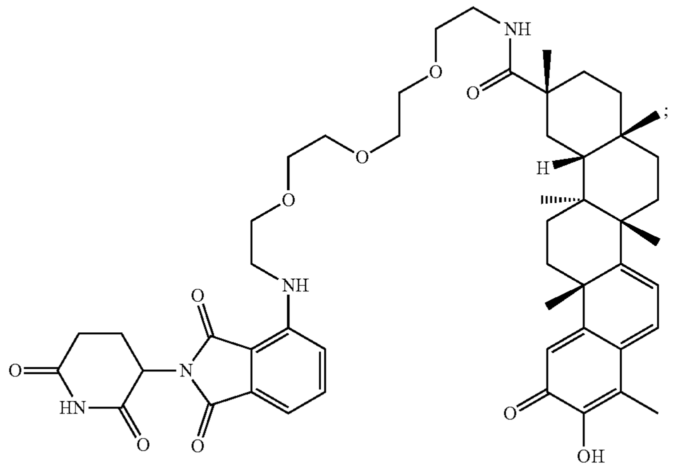
or a pharmaceutically acceptable salt thereof.
In another aspect, provided herein is a compound of Formula (I), or a pharmaceutically acceptable salt thereof:
Formula (I)
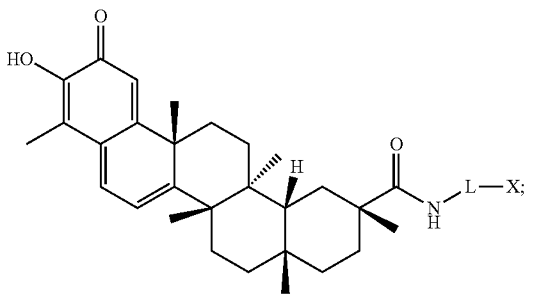
wherein L is $C_{4-8}$ alkylene or $C_{4-9}$ heteroalkylene, wherein $C_{4-9}$ heteroalkylene comprises 1-4 oxygen atoms; and
X is
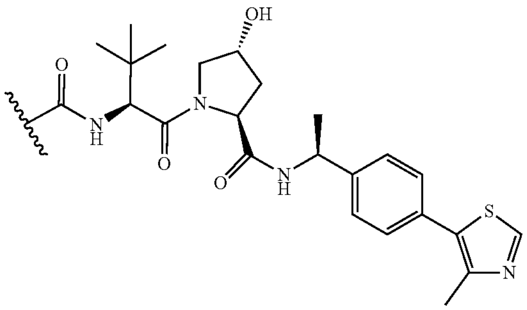
or
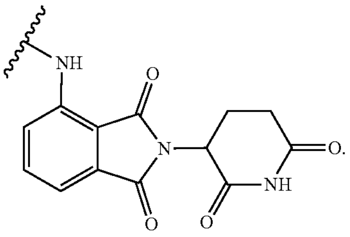

In some embodiments, X is

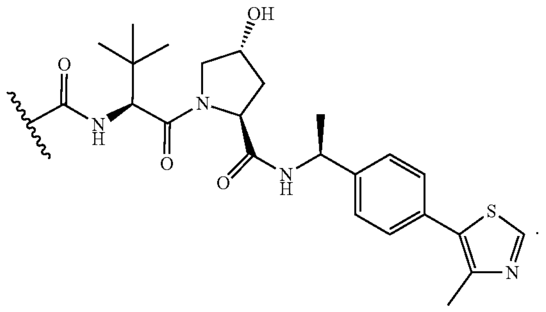 [SMILES: *C(=O)N[C@H](C(=O)N1C[C@H](O)C[C@H]1C(=O)N[C@@H](C)c1ccc(-c2scnc2C)cc1)C(C)(C)C]

In certain embodiments, X is

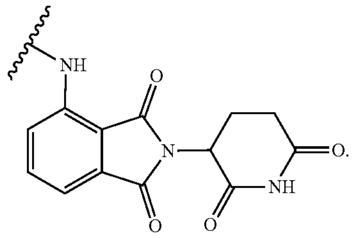

In some embodiments, L is $C_{6-8}$ alkylene or $C_{4-8}$ heteroalkylene, wherein $C_{4-8}$ heteroalkylene comprises 1-4 oxygen atoms In some embodiments, L is $C_{4-8}$ alkylene. In certain embodiments, L is $C_{4-6}$ alkylene. In some embodiments, L is $C_{5-7}$ alkylene. In certain embodiments, L is $C_{6-8}$ alkylene. In some embodiments, L is $C_4$ alkylene. In certain embodiments, L is $C_5$ alkylene. In some embodiments, L is $C_6$ alkylene. In certain embodiments, L is $C_7$ alkylene. In some embodiments, L is $C_8$ alkylene.

In certain embodiments, L is $C_{4-9}$ heteroalkylene, wherein $C_{4-9}$ heteroalkylene comprises 1-4 oxygen atoms. In some embodiments, L is $C_{4-6}$ heteroalkylene, wherein $C_{4-6}$ heteroalkylene comprises 1, 2, 3, or 4 oxygen atoms. In certain embodiments, L is $C_{4-6}$ heteroalkylene, wherein $C_{4-6}$ heteroalkylene comprises 1-2 oxygen atoms. In some embodiments, L is $C_{5-8}$ heteroalkylene, wherein $C_{4-6}$ heteroalkylene comprises 1-2 oxygen atoms. In certain embodiments, L is $C_{7-9}$ heteroalkylene, wherein $C_{7-9}$ heteroalkylene comprises 3-4 oxygen atoms.

In some embodiments, the compound of Formula (I) is NR-V03, NR-V07, NR-V04, NR-V46, NR-V50, NR-C58, NR-C91, NR-C92, or NR-C93. In certain embodiments, the compound of Formula (I) is NR-V04 or NR-C91, or a pharmaceutically acceptable salt thereof. In some embodiments, the compound of Formula (I) is NR-V04, or a pharmaceutically acceptable salt thereof. In certain embodiments, the compound of Formula (I) is NR-C91, or a pharmaceutically acceptable salt thereof.

In another aspect, the provided herein is a pharmaceutical composition comprising a compound described herein (e.g., Formula (I)), or a pharmaceutically acceptable salt thereof, and a pharmaceutically acceptable adjuvant. In some embodiments, the pharmaceutical composition further comprises an additional agent. In certain embodiments, the additional agent is an anti-cancer agent In another aspect, provided herein is a method of treating cancer in a subject, comprising administration of a compound provided herein (e.g., Formula (I)), or a pharmaceutically acceptable salt thereof, to the subject. In some embodiments, the cancer is breast cancer, lung cancer, liver cancer, pancreatic cancer, intestinal cancer, cancer of the spleen, colon cancer, colorectal cancer, melanoma, thyroid carcinoma, esophageal adenocarcinomas, or bladder cancer. In some embodiments, the cancer is breast cancer, lung cancer, liver cancer, pancreatic cancer, intestinal cancer, cancer of the spleen, colon cancer, melanoma, thyroid carcinoma, esophageal adenocarcinomas, or bladder cancer. In certain embodiments, the cancer is breast cancer, lung cancer, thyroid carcinoma, esophageal adenocarcinomas, or bladder cancer. In certain embodiments, the cancer is breast cancer, lung cancer, melanoma, or colorectal cancer. In some embodiments, the cancer is breast cancer, lung cancer, or melanoma. In some embodiments, the subject is a mammal. In certain embodiments, the subject is a human. In some embodiments, the method further comprises administration of an additional anti-cancer agent.

In another aspect, provided herein is a method of treating cancer in a subject identified as in need thereof, comprising administration of a compound provided herein (e.g., Formula (I)), or a pharmaceutically acceptable salt thereof, to the subject. In some embodiments, the cancer is breast cancer, lung cancer, liver cancer, pancreatic cancer, intestinal cancer, cancer of the spleen, colon cancer, colorectal cancer, melanoma, thyroid carcinoma, esophageal adenocarcinomas, or bladder cancer. In some embodiments, the cancer is breast cancer, lung cancer, liver cancer, pancreatic cancer, intestinal cancer, cancer of the spleen, colon cancer, melanoma, thyroid carcinoma, esophageal adenocarcinomas, or bladder cancer. In certain embodiments, the cancer is breast cancer, lung cancer, thyroid carcinoma, esophageal adenocarcinomas, or bladder cancer. In certain embodiments, the cancer is breast cancer, lung cancer, melanoma, or colorectal cancer. In some embodiments, the cancer is breast cancer, lung cancer, or melanoma. In certain embodiments, the subject is a mammal. In some embodiments, the subject is a human. In some embodiments, the method further comprises administration of an additional anti-cancer agent.

In another aspect, provided herein is a method of modulating Nuclear Receptor Subfamily 4 Group A Member 1 (NR4A1) in a subject, comprising administration of a compound provided herein (e.g., Formula (I)), or a pharmaceutically acceptable salt thereof, to the subject.

BRIEF DESCRIPTION OF THE DRAWINGS

The present invention is further described below with reference to the following non-limiting examples and with reference to the following figures, in which:

FIG. 2 depicts the correlation between NR4A1 expression and cancer prognosis.

FIG. 4 shows celastrol-based NR4A1-Ps efficiently degraded NR4A1 at 1 μM, with VHL-based NR-V04 showing the best efficiency in inducing NR4A1 degradation.

FIG. 5 depicts % viability versus concentration of DMSO, celastrol, NT, and NR-V04 in T47D cells (FIG. 5A), MCF7-Tam cells (FIG. 5B), and MCF10A cells (FIG. 5C).

FIG. 6 shows NR4A1 is one of the most elevated gene in TI-Tregs across cancer. FIG. 6B shows Log-Fold change in Y axis and % of difference (TI versus PBMC) in Tregs expressing NR4A1 in X axis. FIG. 6C shows NR4A1 expression in HCC TI-CD8, Tconv, or Tregs. FIG. 6D shows NR4A1 expression in Tregs, Tconv, and CD8 of blood, normal liver, junctional tissues (between normal and cancer tissues) or tumors. Note the at least 5-10 fold more NR4A1 in TI-Tregs than others.

FIG. 7 shows TI-Treg inhibition by NR-04s.

FIG. 10 shows NR-V04 treatment inhibit B16F10 melanoma growth in immunocompetent mice. FIG. 10A and FIG. 10B are the same experiment, but FIG. 10B includes only control vehicle and NR-V04 treated groups in FIG. 10B.

FIG. 13 shows NR-V04 treatment leads to decreased TI-Tregs in several syngeneic tumor models. (FIG. 13B) RENCA renal cancer model, 20 mg/kg once a week for 3 weeks; (FIG. 13C-13D) Py8119 breast cancer model, 8 mg/kg once a week for 3 weeks; with FIG. 13C showing the ratios between Treg/Tconv and FIG. 13D showing Treg/CD8+ T cell ratios.

FIG. 14 shows NR-V04 specifically leads to TI-Treg reduction in human PBMC upon CD3/CD28 co-stimulation. T cells were purified from human PBMC from cancer patients and co-stimulated with anti-CD3/CD28 dynabeads for 3 days, following with DMSO, 500 nM or 1 uM of NR-V04 treatment for two days.

DETAILED DESCRIPTION

Definitions

Figure 1:
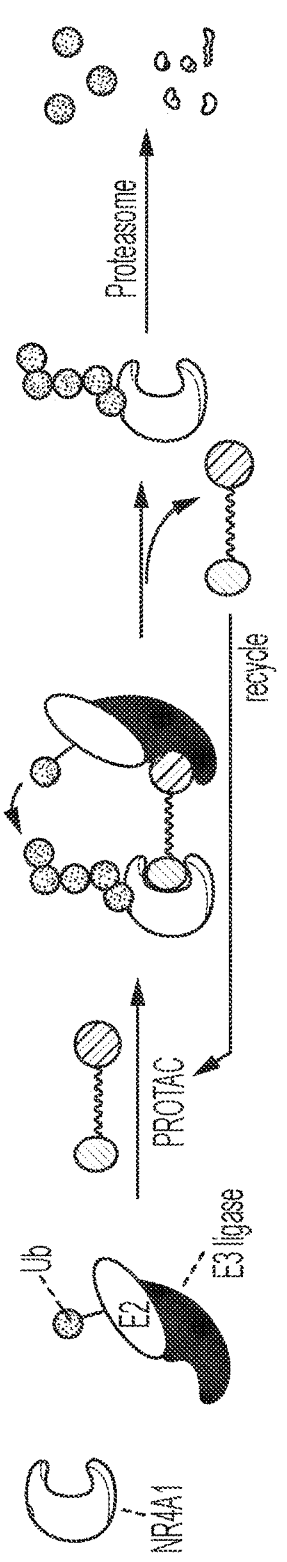
FIG. 1 depicts the mechanism of induced NR4A1 degradation by PROTACs.

In order that the invention may be more readily understood, certain terms are first defined here for convenience.

As used herein, the term “treating” a disorder encompasses ameliorating, mitigating and/or managing the disorder and/or conditions that may cause the disorder. The terms “treating” and “treatment” refer to a method of alleviating or abating a disease and/or its attendant symptoms. In accordance with the present invention, “treating” includes blocking, inhibiting, attenuating, modulating, reversing the effects of and reducing the occurrence of e.g., the harmful effects of a disorder.

As used herein, “inhibiting” encompasses reducing and halting progression.

The term “modulate” refers to increases or decreases in the activity of a cell in response to exposure to a compound of the invention.

The terms “isolated,” “purified,” or “biologically pure” refer to material that is substantially or essentially free from components that normally accompany it as found in its native state. Purity and homogeneity are typically determined using analytical chemistry techniques such as polyacrylamide gel electrophoresis or high-performance liquid chromatography. Particularly, in embodiments the compound is at least 85% pure, more preferably at least 90% pure, more preferably at least 95% pure, more preferably at least 98% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "protein" refers to series of amino acid residues connected one to the other by peptide bonds between the alpha-amino and carboxy groups of adjacent residues.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 μg/kg to about 200 mg/kg, preferably about 0.1 mg/kg to about 200 mg/kg, more preferably about 10 mg/kg to about 100 mg/kg of body weight. In other embodiments, the therapeutically effect amount may range from about 1.0 μM to about 500 nM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 μg/kg to about 200 mg/kg of body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore, the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a $C_1$-$C_6$ alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

"NR4A1" as used herein refers to Nuclear Receptor Subfamily 4 Group A Member 1 protein. NR4A1 belongs to the NR4A nuclear receptor family of intracellular transcription factors. NR4A1 is also known as NUR77, NAK-1, and NGFIB.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Compounds of the Invention

Compounds delineated herein (e.g., Formula I) include salt, hydrate and solvates thereof. They include all compounds delineated in schemes herein, whether intermediate or final compounds in a process.

Compounds of the invention can be obtained from natural sources or made or modified made by means known in the art of organic synthesis. Methods for optimizing reaction conditions, if necessary minimizing competing by-products, are known in the art.

Reaction optimization and scale-up may advantageously utilize high-speed parallel synthesis equipment and computer-controlled microreactors (e.g. *Design And Optimization in Organic Synthesis, 2nd Edition*, Carlson R, Ed, 2005; Elsevier Science Ltd.; Jahnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database. For example, compounds of formulae herein can be made using methodology known in the art, including Doi et al., Org Lett. 2006 Feb. 2; 8(3): 531-4; Ma, et al., Chemistry. 2006 Oct. 10; 12(29):7615-26; and Chen et al., Proc Natl Acad Sci USA. 2004 Aug. 17; 101(33):12067-72.

The compounds herein may also contain linkages (e.g., carbon-carbon bonds) wherein bond rotation is restricted about that particular linkage, e.g., restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. All hydrate and solvate forms of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. All isomers of compounds delineated herein are expressly included in the present disclosure. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

In another aspect, provided herein is a method of treating cancer in a subject, comprising administration of a compound provided herein, or a pharmaceutically acceptable salt thereof, to the subject. In some embodiments, the cancer is breast cancer, lung cancer, liver cancer, pancreatic cancer, intestinal cancer, cancer of the spleen, colon cancer, colorectal cancer, melanoma, thyroid carcinoma, esophageal adenocarcinomas, or bladder cancer. In some embodiments, the cancer is breast cancer, lung cancer, liver cancer, pancreatic cancer, intestinal cancer, cancer of the spleen, colon cancer, melanoma, thyroid carcinoma, esophageal adenocarcinomas, or bladder cancer. In certain embodiments, the cancer is breast cancer, lung cancer, thyroid carcinoma, esophageal adenocarcinomas, or bladder cancer. In certain embodiments, the cancer is breast cancer, lung cancer, melanoma, or colorectal cancer. In some embodiments, the cancer is breast cancer, lung cancer, or melanoma. In some embodiments, the cancer is cancer. In some embodiments, the cancer is breast cancer. In some embodiments, the cancer is lung cancer. In some embodiments, the cancer is colorectal cancer. In some embodiments, the cancer is melanoma. In some embodiments, the method further comprises administration of an additional anti-cancer agent.

In another aspect, provided herein is a method of treating cancer in a subject identified as in need thereof, comprising administration of a compound provided herein, or a pharmaceutically acceptable salt thereof, to the subject. In some embodiments, the cancer is breast cancer, lung cancer, liver cancer, pancreatic cancer, intestinal cancer, cancer of the spleen, colon cancer, colorectal cancer, melanoma, thyroid carcinoma, esophageal adenocarcinomas, or bladder cancer. In some embodiments, the cancer is breast cancer, lung cancer, liver cancer, pancreatic cancer, intestinal cancer, cancer of the spleen, colon cancer, melanoma, thyroid carcinoma, esophageal adenocarcinomas, or bladder cancer. In certain embodiments, the cancer is breast cancer, lung cancer, thyroid carcinoma, esophageal adenocarcinomas, or bladder cancer. In certain embodiments, the cancer is breast cancer, lung cancer, melanoma, or colorectal cancer. In some embodiments, the cancer is breast cancer, lung cancer, or melanoma. In some embodiments, the cancer is breast cancer. In some embodiments, the cancer is lung cancer. In some embodiments, the cancer is colorectal cancer. In some embodiments, the cancer is melanoma. In some embodiments, the method further comprises administration of an additional anti-cancer agent.

In another aspect, provided herein is a method of modulating Nuclear Receptor Subfamily 4 Group A Member 1 (NR4A1) in a subject, comprising administration of a compound provided herein, or a pharmaceutically acceptable salt thereof, to the subject.

Non-limiting examples of neoplasms or cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas, breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, choriocarcinoma, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, glioblastoma, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In certain embodiments, a cancer is selected from the group consisting of synovial sarcoma, Burkitt lymphoma, Hodgkin lymphoma, multiple myeloma, neuroblastoma, glioblastoma, small cell lung cancer, pancreatic cancer, hepatocellular (liver) cancer, endometrial cancer, ovarian cancer, cervical cancer, breast cancer, prostate cancer, bladder cancer, melanoma, rhabdomyosarcoma, osteosarcoma/malignant fibrous histiocytoma of bone, choriocarcinoma, kidney cancer (renal cell cancer), thyroid cancer, and leukemias (acute lymphoblastic, acute myeloid, chronic lymphocytic, and chronic myelogenous).

Pharmaceutical Compositions

In another aspect, provided herein is a pharmaceutical composition comprising a compound provided herein, or a pharmaceutically acceptable salt thereof, and a pharmaceutically acceptable adjuvant.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

In certain embodiments, the composition further comprises an additional agent. In some embodiments, the additional agent is an anti-cancer agent. In certain embodiments, the anticancer agent is alkylating agent, an anti-metabolite, an anti-tumor antibiotic, an anti-cytoskeletal agent, a topoisomerase inhibitor, an anti-hormonal agent, a targeted therapeutic agent, a photodynamic therapeutic agent, or a combination thereof.

Non-limiting examples of suitable alkylating agents include altretamine, benzodopa, busulfan, carboplatin, carboquone, carmustine (BCNU), chlorambucil, chlornaphazine, cholophosphamide, chlorozotocin, cisplatin, cyclosphosphamide, dacarbazine (DTIC), estramustine, fotemustine, ifosfamide, improsulfan, lipoplatin, lomustine (CCNU), mafosfamide, mannosulfan, mechlorethamine, mechlorethamine oxide hydrochloride, melphalan, meturedopa, mustine (mechlorethamine), mitobronitol, nimustine, novembichin, oxaliplatin, phenesterine, piposulfan, prednimustine, ranimustine, satraplatin, semustine, temozolomide, thiotepa, treosulfan, triaziquone, triethylenemelamine, triethylenephosphoramide (TEPA), triethylenethiophosphaoramide (thiotepa), trimethylolomelamine, trofosfamide, uracil mustard and uredopa.

Suitable anti-metabolites include, but are not limited to aminopterin, ancitabine, azacitidine, 8-azaguanine, 6-azauridine, capecitabine, carmofur (1-hexylcarbomoyl-5-fluorouracil), cladribine, clofarabine, cytarabine (cytosine arabinoside (Ara-C)), decitabine, denopterin, dideoxyuridine, doxifluridine, enocitabine, floxuridine, fludarabine, 5-fluorouracil, gemcitabine, hydroxyurea (hydroxycarbamide), leucovorin (folinic acid), 6-mercaptopurine, methotrexate, nafoxidine, nelarabine, oblimersen, pemetrexed, pteropterin, raltitrexed, tegofur, tiazofurin, thiamiprine, tioguanine (thioguanine), and trimetrexate.

Non-limiting examples of suitable anti-tumor antibiotics include aclacinomysin, aclarubicin, actinomycins, adriamycin, aurostatin (for example, monomethyl auristatin E), authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, epoxomicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, sparsomycin, streptonigrin, streptozocin, tubercidin, valrubicin, ubenimex, zinostatin, and zorubicin.

Non-limiting examples of suitable anti-cytoskeletal agents include cabazitaxel, colchicines, demecolcine, docetaxel, epothilones, ixabepilone, macromycin, omacetaxine mepesuccinate, ortataxel, paclitaxel (for example, DHA-paclitaxel), taxane, tesetaxel, vinblastine, vincristine, vindesine, and vinorelbine.

Suitable topoisomerase inhibitors include, but are not limited to, amsacrine, etoposide (VP-16), irinotecan, mitoxantrone, RFS 2000, teniposide, and topotecan.

Non-limiting examples of suitable anti-hormonal agents such as aminoglutethimide, antiestrogen, aromatase inhibiting 4(5)-imidazoles, bicalutamide, finasteride, flutamide, fluvestrant, goserelin, 4-hydroxytamoxifen, keoxifene, leuprolide, LY117018, mitotane, nilutamide, onapristone, raloxifene, tamoxifen, toremifene, and trilostane.

Examples of targeted therapeutic agents include, without limit, monoclonal antibodies such as alemtuzumab, cartumaxomab, edrecolomab, epratuzumab, gemtuzumab, gemtuzumab ozogamicin, glembatumumab vedotin, ibritumomab tiuxetan, reditux, rituximab, tositumomab, and trastuzumab; protein kinase inhibitors such as bevacizumab, cetuximab, crizonib, dasatinib, erlotinib, gefitinib, imatinib, lapatinib, mubritinib, nilotinib, panitumumab, pazopanib, sorafenib, sunitinib, toceranib, and vandetanib;

Angiogenesis inhibitors such as angiostatin, bevacizumab, denileukin diftitox, endostatin, everolimus, genistein, interferon alpha, interleukin-2, interleukin-12, pazopanib, pegaptanib, ranibizumab, rapamycin (sirolimus), temsirolimus, and thalidomide; and growth inhibitory polypeptides such as bortazomib, erythropoietin, interleukins (e.g., IL-1, IL-2, IL-3, IL-6), leukemia inhibitory factor, interferons, romidepsin, thrombopoietin, TNF-$\alpha$, CD30 ligand, 4-1BB ligand, and Apo-1 ligand.

Non-limiting examples of photodynamic therapeutic agents include aminolevulinic acid, methyl aminolevulinate, retinoids (alitretinon, tamibarotene, tretinoin), and temoporfin.

Other antineoplastic agents include anagrelide, arsenic trioxide, asparaginase, bexarotene, bropirimine, celecoxib, chemically linked Fab, efaproxiral, etoglucid, ferruginol, lonidamide, masoprocol, miltefosine, mitoguazone, talapanel, trabectedin, and vorinostat.

In one aspect, provided herein is a kit comprising an effective amount of a compound provided here (e.g., Formula (I)), in unit dosage form, together with instructions for administering the compound to a subject suffering from or susceptible to cancer. In some embodiments, the cancer is breast cancer, lung cancer, liver cancer, pancreatic cancer, intestinal cancer, cancer of the spleen, colon cancer, colorectal cancer, melanoma, thyroid carcinoma, esophageal adenocarcinomas, or bladder cancer. In some embodiments, the cancer is breast cancer, lung cancer, liver cancer, pancreatic cancer, intestinal cancer, cancer of the spleen, colon cancer, melanoma, thyroid carcinoma, esophageal adenocarcinomas, or bladder cancer. In certain embodiments, the cancer is breast cancer, lung cancer, thyroid carcinoma, esophageal adenocarcinomas, or bladder cancer. In certain embodiments, the cancer is breast cancer, lung cancer, melanoma, or colorectal cancer. In some embodiments, the cancer is breast cancer. In some embodiments, the cancer is lung cancer. In some embodiments, the cancer is colorectal cancer. In some embodiments, the cancer is melanoma. In some embodiments, the cancer is breast cancer, lung cancer, or melanoma.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

EXAMPLES

The present invention will now be demonstrated using specific examples that are not to be construed as limiting.

Without wishing to be bound by a particular theory, Applicants posit that NR4A1 plays lineage-specific roles in breast cancer and provides a critical transcriptional network that is essential to promote the invasiveness/metastasis of cancer cells, simultaneously leading to immune suppression by leading to the exhaustion/dysfunction of CD8 T cells and maintaining the function of TI-Tregs. Therefore, targeting NR4A1 can increase anti-cancer immunity by selective inhibition of TI-Tregs and activation of CD8 T cells, as well as directly inhibit cancer cell invasiveness and metastasis. PROTAC is an enabling technology that can transform weak NR4A1 ligands into potent and long-lasting degraders.

Figure 2A:
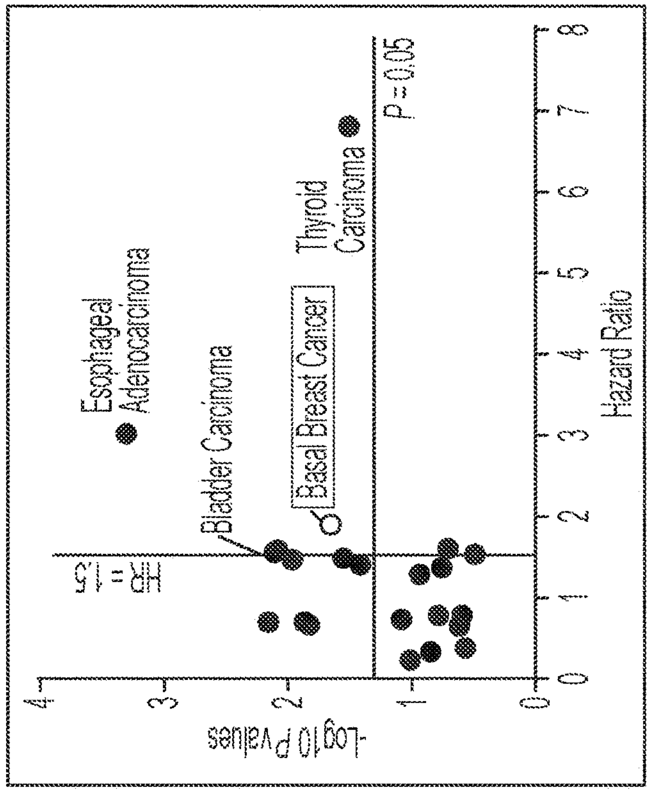
FIG. 2A. TCGA RNAseq data of 21 cancer types were analyzed for the correlation of NR4A1 with overall survival, showing hazard ratio and −Log 10 P values.
Figure 2B:
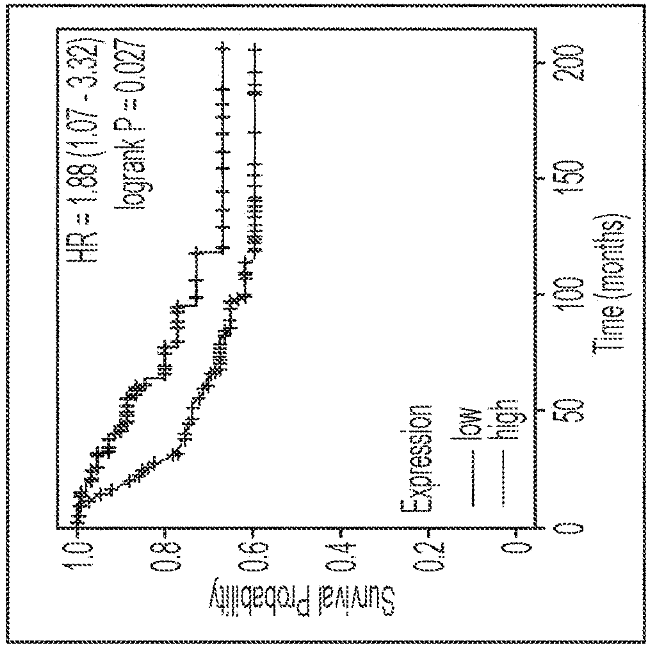
FIG. 2B. NR4A1 expression is inversely correlated with overall survival time in basal like breast cancer. Hazard ratio (HR)=1.88. P=0.027.

Description of Supporting Data:

NR4A1 in cancer prognosis. Using TCGA datasets, the correlation was determined between NR4A1 expression and overall survival (OS) of 21 major cancer types (FIG. 2A). While NR4A1 mRNA has no predictive value for most cancer types, higher NR4A1 is correlated with shorter OS in basal breast cancer, esophageal adenocarcinoma, thyroid carcinoma and bladder carcinomas (FIG. 2A), with basal breast cancer showing hazard ratio of 1.88 (FIG. 2B). The other two cancers include esophageal adenocarcinoma and thyroid carcinoma where NR4A1 expression is clearly associated with poor prognosis (FIG. 2A). The analysis agrees with published results (12), altogether supporting the critical role of NR4A1 in cancer progression from several cancer types.

Figure 3:
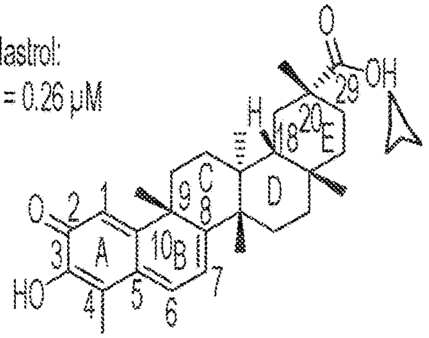
FIG. 3 depicts example chemical structures for NR4A1-Ps, including CRBN-based NR-C91 and VHL-based NR-V04. Celastrol, linkers, and CRBR or VHL ligands are shown.
Figure 3:
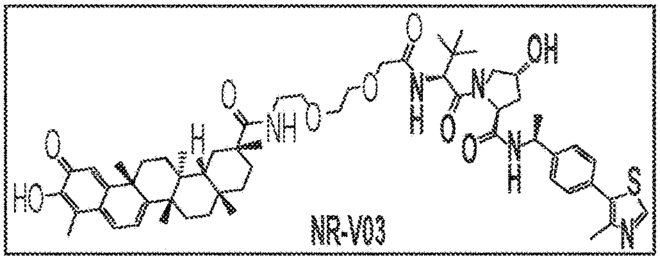
Figure 3:
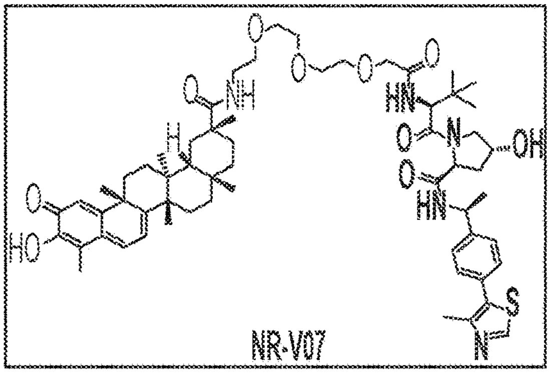
Figure 3:
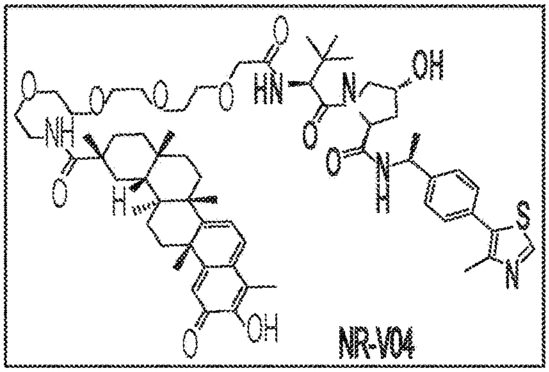
Figure 3:
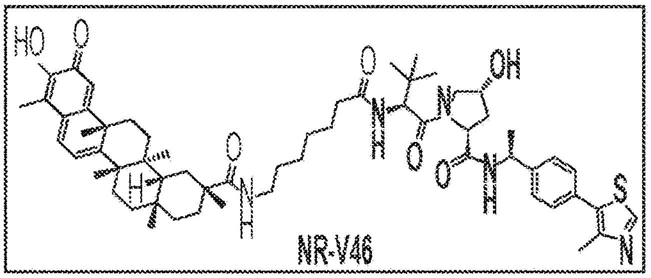
Figure 3:
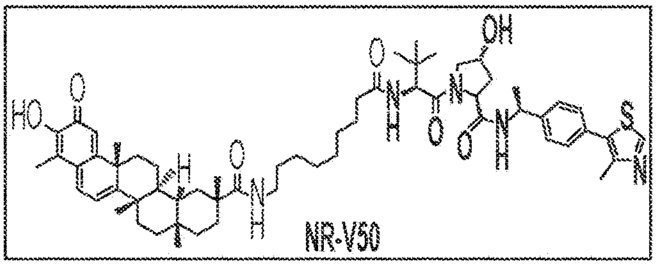
Figure 3:
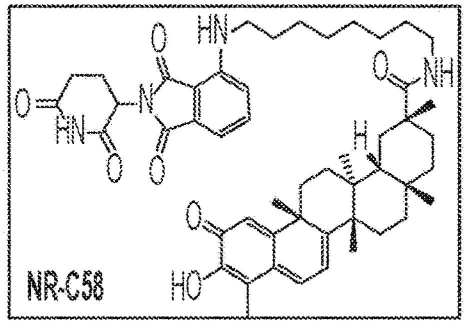
Figure 3:
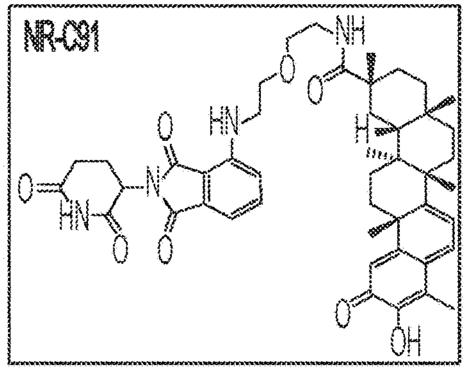
Figure 3:
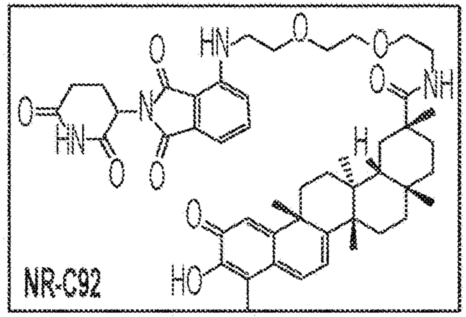
Figure 3:
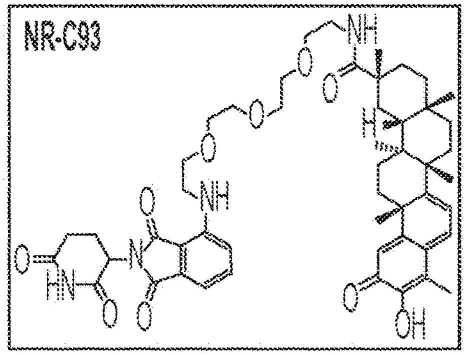
Figure 4A:
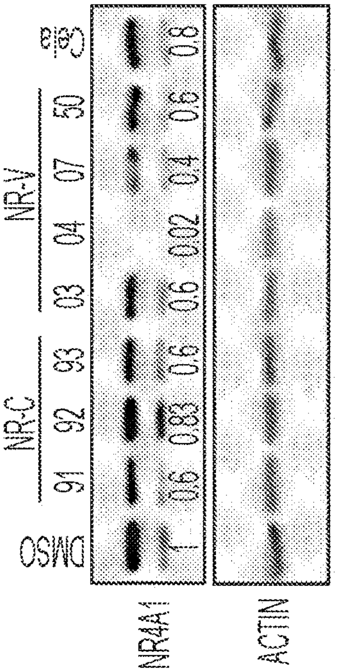
FIG. 4A. Efficiency of NR4A1-Ps in protein degradation using 3 examples of NR4A1-Ps based on CRBN (NR-C91, 92, 93) and 4 based on VHL (NR-V03, 04, 07, 50), with NR-V04 showing the best efficacy in NR4A1 degradation.
Figure 4B:
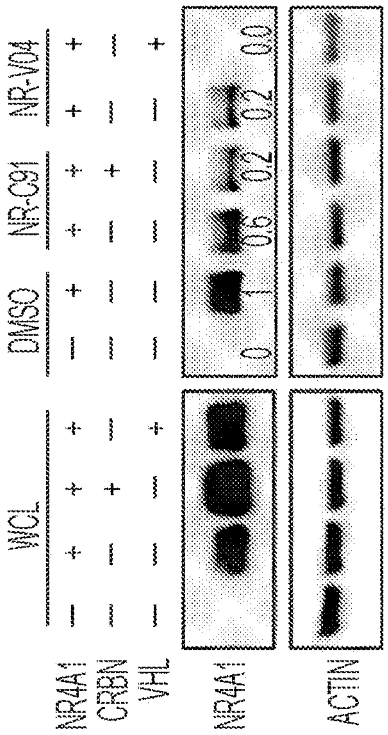
FIG. 4B. NR4A1 degradation is mediated by targeted E3 ligases. HEK293T cells were transfected with NR4A1, with or without overexpression of CRBN or VHL. 36 hrs after transfection, cells were treated with 3 μM of NR-C91 or NR-V04 for 6 hrs for immunoblotting.
Figure 9:
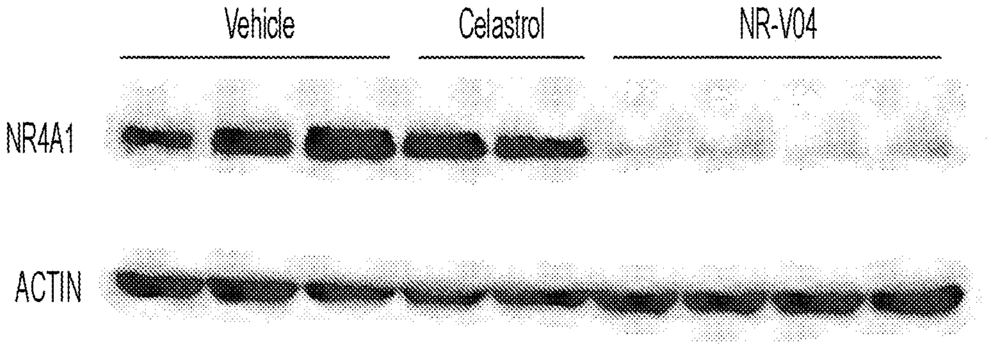
FIG. 9 shows NR-V04 leads to NR4A1 degradation in tumor models. MC38-tumor bearing mice were treated with 0.75 mg/kg celastrol or 1.8 mg/kg NR-V04, twice weekly for 3 weeks. Tumor lysates were used for immunoblotting.

Developing NR4A1-Ps. Due to the diverse function of NR4A1 in different cancer types, both agonistic and antagonistic ligands of NR4A1 are of interest in development (25). Two NR4A1 ligands were selected, cytosporone-B (Kd=1.68 μM) (26, 27) and celastrol (Kd=0.28 μM) (28, 29), as 'warhead' and were linked with either a VHL or a CRBN E3 ligase ligand. 4 cytosporone-B-based and 10 celastrol-based NR4A1-Ps using polyethylene glycol (PEG) linkers of various length have already been synthesized (FIG. 3 showing several examples). None of the cytosporone-B-based NR4A1-Ps were able to degrade endogenous NR4A1 in T47D breast cancer cells, likely due to the poor binding affinity of the warhead to NR4A1; whereas several celastrol-based NR4A1-Ps (FIG. 3 showing several examples) efficiently degraded NR4A1 at 1 μM, with VHL-based NR-V04 showing the best efficiency in inducing NR4A1 degradation (FIG. 4A, including three CRBN-based NR-C91, 92, and 93 and four VHL-based NR-V03, 04, 07, and 50). CRBN-based NR-C91 also led to the degradation of NR4A1, but not as efficiently as NR-V04. Two example PROTACs, including CRBN-based NR-C91 and VHL-based NR-V04, were included and further showed that overexpression of their corresponding E3 ligases facilitated NR4A1-P-mediated degradation of NR4A1 (FIG. 4B). It was further confirmed that NR-V04 leads to efficient degradation of target protein NR4A1 within mouse MC38 tumors when treated in tumor-bearing mice (FIG. 9).

Figure 5A:
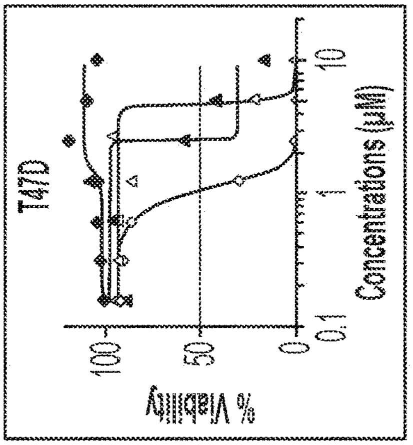
FIG. 5 shows NR4A1-Ps kill breast cancer cells directly.
Figure 5B:
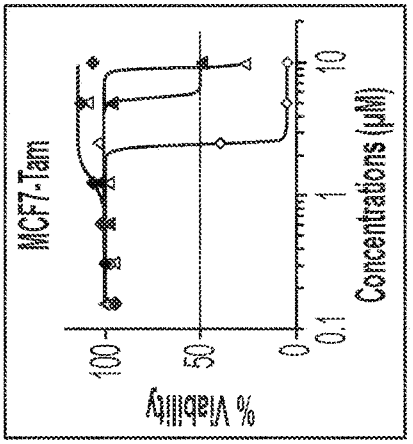
Figure 5C:
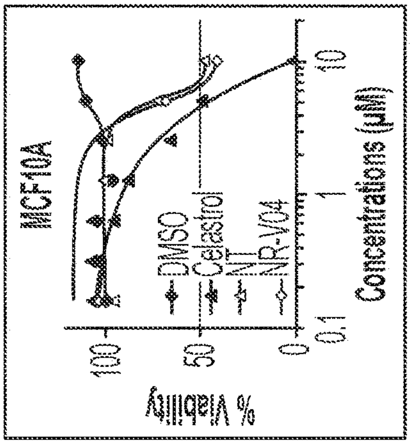

NR4A1-Ps selectively kill breast cancer cells. Since NR-V04 is very efficient in NR4A1 degradation, a negative control, NR-V04-NT, was synthesized. NR-V04-NT is structurally very similar to NR-V04 except it does not bind VHL. Treating NR4A1-positive breast cancer cells with NR-V04 leads to a more robust killing relative to celastrol or NR-V04-NT by MTS assay (FIG. 5A-B); whereas NR-V04 is less toxic to MCF10A, an immortalized normal human breast epithelial cells than celastrol (FIG. 5C).

Figure 6B:
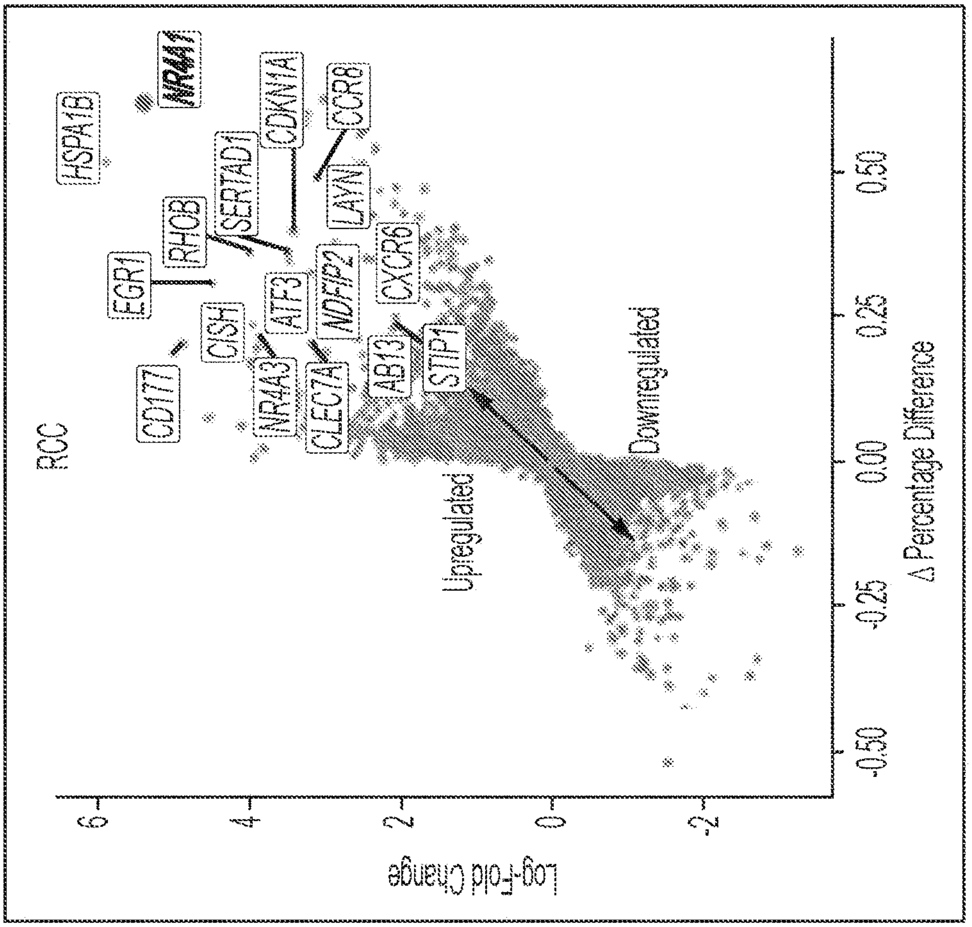
FIG. 6B-6D. Single cell RNAseq of renal cell carcinoma (FIG. 6B, RCC) or human hepatocellular carcinomas (FIG. 6C-6D, HCC) showing NR4A1 as the most upregulated gene in TI-Tregs of both cancer types.
Figure 6A:
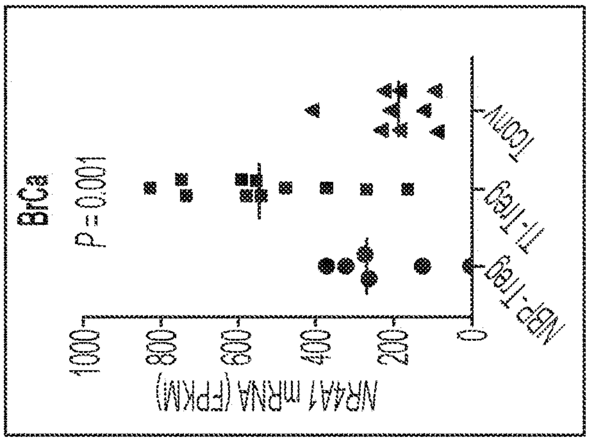
FIG. 6A. Bulk RNAseq of Tregs from normal breast parenchyma (NBP) and tumor-infiltrating (TI), or of TI-non-Treg CD4 T cells (Tconv) from a published dataset (GSE89225).
Figure 6D:
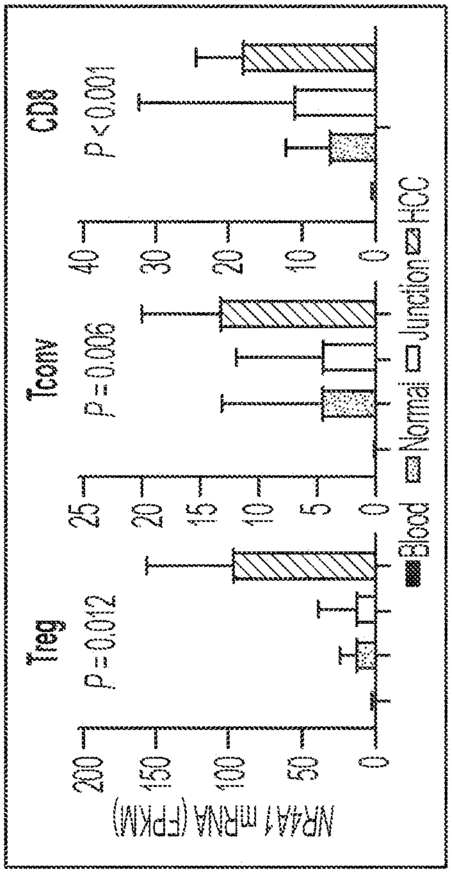
Figure 6C:
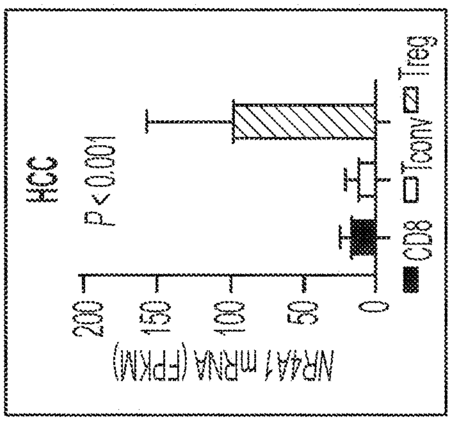

NR4A1 is expressed by TI-Tregs and exhausted CD8 T cells within the TME. NR4A1 was identified as an orphan nuclear receptor that is important for T cell development (18, 19). T cells are at the center of cancer immunotherapy and recently NR4A1 was reported to be one of the most critical factors that induces the exhaustion of CD8 T cells during immunotherapy (8, 9). Since immunotherapy has been approved for TNBC (30), analysis of NR4A1 in T cell subpopulations was expanded. Breast cancer TI-Tregs exhibit significantly elevated NR4A1 expression in a recently published dataset GSE89225 (31) (FIG. 6A). Using the newly developed single cell RNAseq of immune cells from 3 paired PBMC and ccRCC cancer specimens (GEO Access: GSE98638) with preprints (32, 33), a total of 25,672 immune cells passed quality control with 13,433 PBMC and 12,239 cancer-infiltrating immune cells. tNSE plot defined a total of 22 clusters, including 1 cluster of Tregs (160 PBMC Tregs and 574 TI-Tregs (32, 33). NR4A1 was the most upregulated gene in TI-Tregs of renal cell carcinoma (RCC) (45), comparing with paired PBMC-Tregs (FIG. 6B), and dramatically elevated in TI-Tregs in a recently published single cell RNAseq datasets of human liver cancers (34) (FIG. 6C-D). Preliminary analysis strongly supports that NR4A1 upregulation in TI-Tregs is a common feature in other cancers as well. TI-CD8 T cells also have elevated NR4A1 expression in HCC (FIG. 6D).

Overall Rationale: NR4A1 clearly stands out from other drug targets due to its various functions in cancer cells, exhausted CD8 T cells, and TI-Tregs. NR4A1 expression is correlated with shorter overall survival within basal breast cancer, thyroid carcinoma, esophageal adenocarcinomas and bladder cancers, but overall is not predictive of patient survival among most other cancer types (FIG. 2A). Since the high cancer cell content from these bulk RNAseq of TCGA datasets (most with at least 60% nuclei from cancer cells), the prognostic data is only indicative of its potential function in cancer cells. Other cancers may also benefit from therapeutic intervention of NR4A1 due to the role NR4A1 in immune modulation such as inducing PD-L1 expression, an immune checkpoint that induces exhaustion of CD8 T cells in TME (10) and enhancing Treg function (21). Hence, antagonizing NR4A1 not only can suppress cancer progression directly, but also elicit an immune active TME by rejuvenating CD8 activation. Even though NR4A1 is shown to be involved in clonal depletion of thymic/natural Tregs (20, 35), the function of NR4A1 in TME seems to be opposite since deletion of NR4A1 family in CD4 T cells led to decreased TI-Tregs (21), supporting the critical role of NR4A1 in TI-Treg function (FIG. 6). The triple actions of NT4A1 make it an ideal target for cancer therapy. However, the available NR4A1 inhibitors are not sufficiently potent for clinical translation and increasing their potency through structural optimization might be challenging because of the shallow binding pocket on NR4A1. State-of-the-art PROTAC technology will be used to design a first-of-its-kind potent and specific NR4A1 degrader, i.e., NR4A1-P, for clinical development into breast cancer therapeutic.

Determination of on- and off-target toxicities of lead NR4A1-Ps;

SA1.1: In vitro evaluation of NR4A1-Ps. For all the newly designed/synthesized NR4A1-Ps, using NR-V04 as an example, biochemical experiments will be performed to determine NR4A1-degradation efficiency using HEK293T cells with Flag-NR4A1 expression as in FIG. 4B with a dose range from 10 nM to 10 μM; cytotoxicity assays to determine $EC_{50}$ for cell viability using T47D and MCF7-Tam cells with endogenous NR4A1 (FIG. 5). A CRISPR/Cas9-mediated knock out (KO) of NR4A1 will be constructed from these two cells to determine if the NR4A1-Ps differentially kill NR4A1 WT cells but not KO cells that can survive based on literature. All the new compounds will be compared side-by-side with NR-V04, NR-C91, celastrol. For lead compounds showing desirable NR4A1-degradation efficiency, the binding efficiency of new NR4A1-Ps will be characterized in comparison to celastrol; ternary complex formation will be determined among NR4A1, NR4A1-Ps, and VHL/CRBN E3 ligase using AlphaLISA assay per established protocol; the specificity in degradation of NR4A1 will be determined by proteome profiling using SILAC cellular expression proteomics assay in comparison with relative non-targeting control in T47D or HEK293T cells with expression of NR4A1; VHL or CRBN dependency will be confirmed by using their relevant KO cells.

SA1.2: In vivo preclinical determination of the maximal tolerated dose and toxicity. Each lead NR4A1-P including NR-V04 will be initially tested for in vitro stability in mouse and human liver microsomes and hepatocytes, followed by a preliminary in vivo PK study in mice with IP and IV dosing. PK studies will be done by the UF Translational Drug Development (TDD) Core, including additional tests and choice of a proper treatment regimen (dosing, frequencies and duration of the treatment). The regimen can be used to ensure that an effective dose of the lead compound can be achieved and maintained among various tissues. NR-V04 will be used as an example to determine the toxicity and maximal tolerated doses in WT and NR4A1 knockout mouse (currently breeding in the lab), in comparison with celastrol with reported ranges from daily 0.1 mg/kg to 8 mg/kg (37). At least 3 male and 3 females will be included in each treatment groups, for weekly whole blood counts, terminal histology of all vital organs, and other on-target inflammatory parameters such as the plasma IL-6, TNFα, IL-1 etc., up to at least 4-5 months of window. 3-4 leads for celastrol- and DIM-C-pPhOH-based NR4A1-Ps with improved NR4A1 degradation efficiency for the preliminary PK/toxicity studies will be chosen. The most effective NR4A1-Ps with the least toxicity will be further used for the above tumor studies.

These routine experiments are very inclusive in terms of validating in vivo and in vitro specificity, efficacy, and toxicity for newly synthesized NR-V04. Protein targets for NR4A1-Ps can be validated, including binding efficiency, specificity and target degradation. Knockout mice and cells can be used to compare with all related phenotypes to determine if it is on-target or off-target effects.

Determination of the Antitumor Activities and Immune Modulation.

Figure 7A:
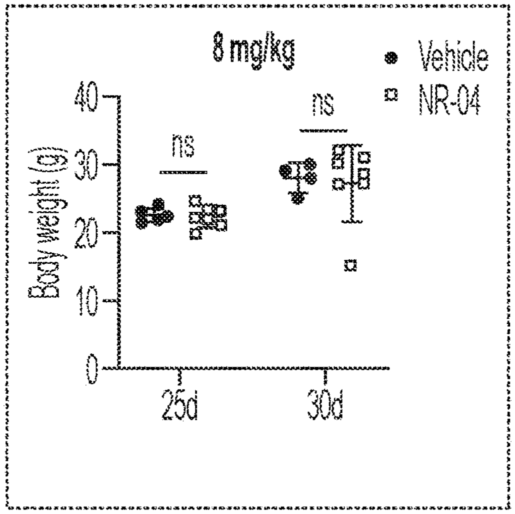
FIG. 7A-FIG. 7D. Py8119 cells were injected into #4 mammary fatpad of 8-week female C57/BL6 mice, following with vehicle or NR-V04 treatment i.p. at 8 mg/kg weekly, starting at day 15 after tumor cell injection. Body weight (FIG. 7A), tumor growth (data not shown), and immune cell profiling by flow cytometry from spleen, tumor, and blood were shown (FIG. 7B-7D). CD45+CD3+CD8+ T cells (FIG. 7B), CD45+CD3+CD4+T (FIG. 7C), and ratios of CD4+Foxp3+ Tregs to total T cells (T), to total CD4 T cells (CD4), to total CD4conv (non Treg CD4 T cells), or to CD8 T cells (FIG. 7D) were shown. * $P<0.05$; ** $P<0.01$.
Figure 7B:
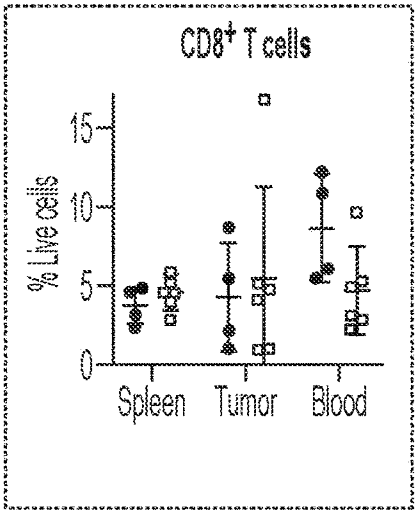
Figure 7C:
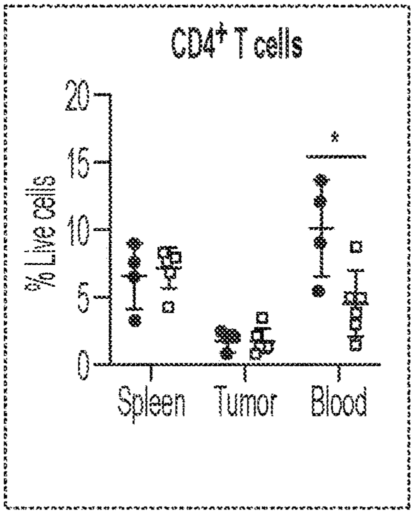
Figure 7D:
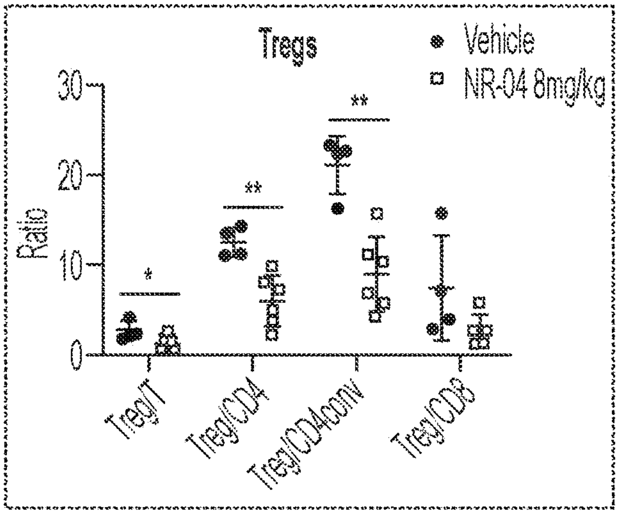

Syngeneic models for antitumor activities. Syngeneic tumor models include breast cancer models: 1) E0771 as luminal breast cancer (C57BL/6 background) (36-38), 2) Py8119 (C57BL/6) (37, 39, 40) and 3) 4T1 (Balb/C) (41, 42) as triple negative breast cancer, and 4) MT2 as HER2-positive breast cancer (FVB/N) (43, 44), all of which develop metastasis upon orthotopic tumor injections; 5) MC-38 colon cancer model; 6) Renca renal carcinoma model; 7) B16 melanoma models. MC-38 is known to be responsive to ICIs and Renca is known to respond of Treg suppression in their tumor growth. B16 is only partially responsive to ICI treatment when anti-CTLA-4 and anti-PD-1 are combined. Careful titration of the minimal cell numbers provides consistent tumor growth and/or metastasis. For testing the efficacy of NR-V04 or other leads, tumor-bearing mice will be treated with either non-targeting NR-V04-NT or NR-V04, or other leads, starting 14 days after tumor cell injection when 3-5 mm in diameter tumor growth is typically seen in all models. The dose and frequency will be used based on the data from SA1.2. Based on work on BCL-$X_L$ PROTAC (22), weekly injection of the leads should be sufficient to maintain effective doses in various tissues. The Py8119 model was used for initial assessment of immune modulations by NR-V04, using an estimate dose of 8 mg/kg, weekly injection of NR-V04 or vehicle (FIG. 7), where there is no difference in body weight at day 25 or 30 after treatment (FIG. 7A). Tumor growth difference was not observed, likely due to the very late treatment (day 15 after tumor injection) and rapid tumor growth (day 30 after only two rounds of treatments) between control and NR-V04-treated groups. On-target decrease of tumor-infiltrating Tregs versus effector T cell ratio was observed, without influencing overall CD4+ and CD8+ T cells (FIG. 7B-D).

Figure 8:
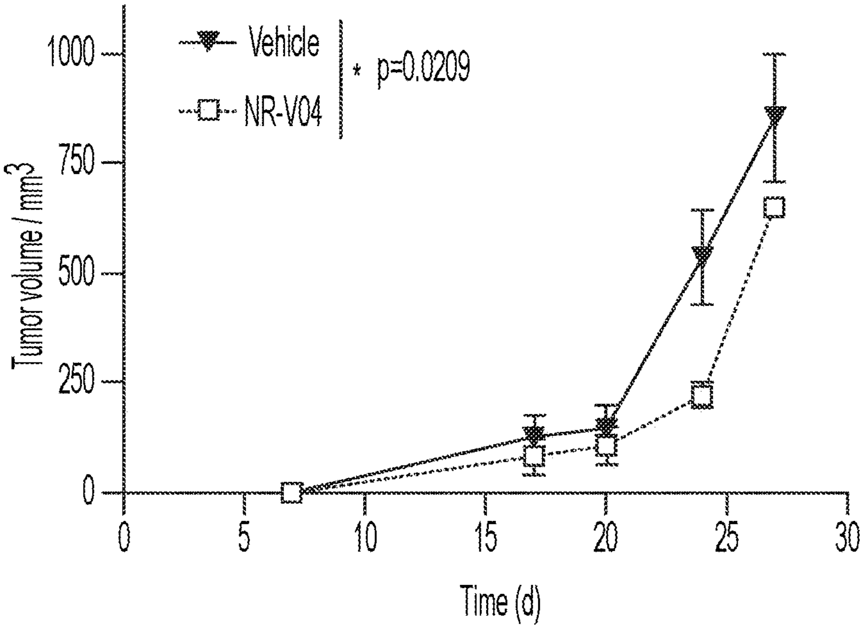
FIG. 8 shows tumor inhibition by NR-04s. RENCA cells (10,000 per injection) were injected into s.c. of 8-week Balb/C mice, following with vehicle or NR-V04 treatment i.p. at 8 mg/kg weekly, starting at day 15 after tumor cell injection. Tumor volume was recorded.

Some of the above tumor models will be included, initially using immune responsive tumors including RENCA and MC38 model. Initial ongoing experiments in RENCA tumor model show significant reduction in the NR-V04-treated group (FIG. 8), and the following parameters will be continued to be recorded for this experiment and all other new experiments. Tumor volumes will be determined twice weekly by a caliper and calculated as length×width$^2$×0.5. Animal will be terminated once the largest tumors reach 2 cm in diameter per IACUC protocol (size is justified to determine lung metastasis).

The parameters include:

Primary tumors—Tumors will be cut into pieces and used for: a) immunohistochemical (IHC) staining (embedding in OCT compound and freezing). Sections will be stained with hematoxylin & eosin (H&E) for pathological evaluation of invasiveness and overall immune infiltrations; for Ki-67 to calculate the proliferative index; for Caspase 3 and TUNEL, to assess apoptosis; and for CD31 staining to evaluate angiogenesis (40). b) preparation of RNA and protein (snap freezing in liquid nitrogen) to determine expression of NR4A1; and c) 200 mg per tumors will be used for immunoprofiling using flow cytometry in Aim 3.

Lung sample—Lungs will be collected for fixation and paraffin embedding. Paraffin sections will be used for H&E staining of step sections (4 sections per lung, at 100 μm intervals) and counting metastatic nodules as done before (43, 44).

Lung, liver, intestine, and pancreas—Even though NR4A1-inhibition is believed to only impact tumor-specific immunity, these tissues will be collected routinely for H&E assessment for potential tissue damage or autoimmune like reactions due to unwanted T cell activation.

These syngeneic tumor models allow evaluation of whether NR-V04 is able to suppress tumor growth and metastasis.

Validation of NR4A1 as valuable target within different cell populations;

Tumor, blood, spleen and draining and non-draining LN—tumor models (including from above) will be evaluated using flow cytometry for immune cells for all relevant tissues.

From tumor, blood, LN, and spleen, flow cytometry protocol will be run on an Aurora Cytek: including fixable viability dye-eFluor 780; CD45 for all immune cells; CD3, CD4, CD8 for T lineages; CD25, FoxP3 for Tregs; CD69, CD62L for naïve/activation; PD-1, Tim-3 for exhaustion; CD107a, Granzyme B for CD8 activation; CD49b for NK; CD11b for myeloid; CD11c, MHCII for DC; Ly-6G, Ly-6C for granulocytic or monocytic; F4/80 for TI macrophages; NR4A1 for on-target deletion.

These immune profiling experiments will allow determination of whether NR4A1-Ps target specific immune populations within tumor microenvironment to boost anti-cancer immunity.

Statistical Plan: Mouse models will be expected to vary by one standard deviation, 1-fold change and a fixed power of 0.8. 17 mice/per group will be the minimal number. For other experiments, a variation of 0.5 standard deviation and 1-fold change is expected, giving 6-7/group. Final products will reach ≥98% purity. The non-parametric Mann-Whitney U test will be used for two groups and Kruskal-Wallis test will be used for more than two groups, unpaired Welch's t test will be used for large datasets for two groups, ANOVA test will be used for more than two groups. Logrank test will be used for all Kaplan-Meier curves. P values≤0.05 will be considered statistically significant.

NR-V04 Exhibits Superior Tumor Inhibitory Effect to Celastrol with Low Toxicity to the Mice.

Figure 10A:
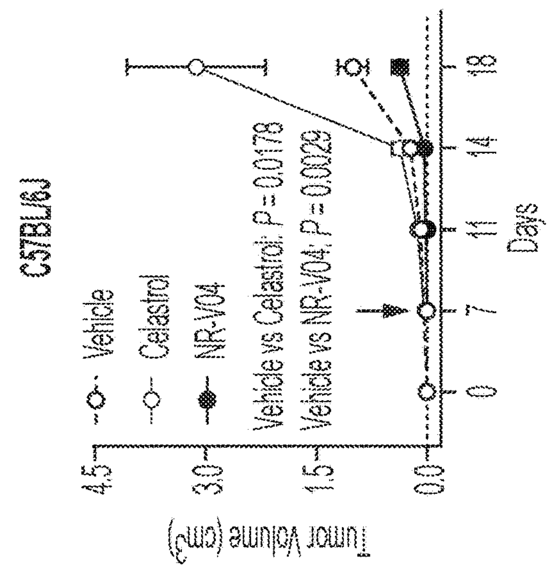
FIG. 10A-10C. B16F10-tumor bearing mice were treated with control vehicle, 0.75 mg/kg celastrol or 1.8 mg/kg NR-V04 (twice weekly for 3 weeks)—7 days after sc injection of 10,000 B16/F10 cells either into C57BL/6J (FIG. 10A-10B) or NSG (FIG. 10C) male mice. Tumor growth were monitored via palpation. N=7 mice/group.
Figure 10B:
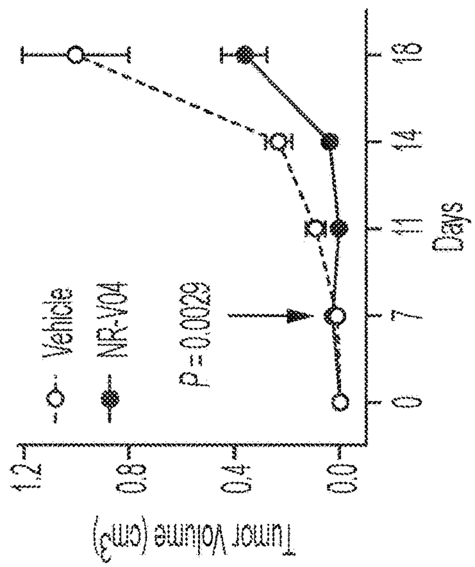
Figure 10C:
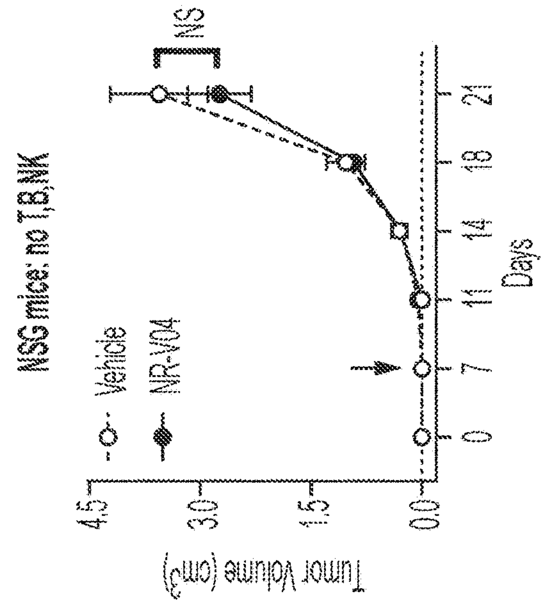
Figure 11:
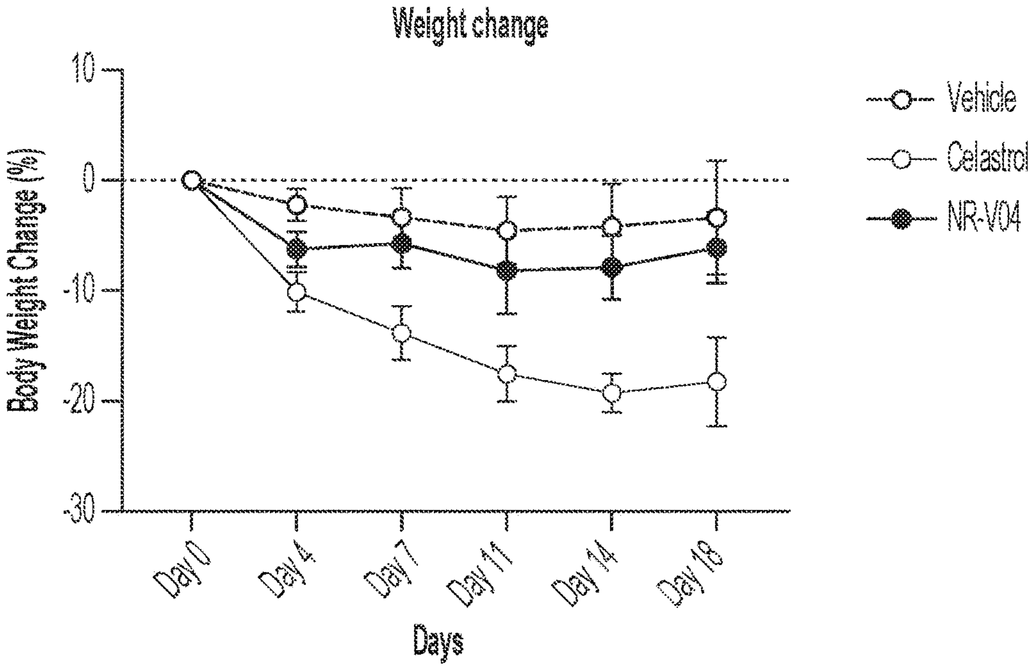
FIG. 11 shows NR-V04 does not reduce body weight. MC38-tumor bearing mice were treated with 0.75 mg/kg celastrol or 1.8 mg/kg NR-V04, twice weekly for 3 weeks. Body weight was recorded weekly.
Figure 12A:
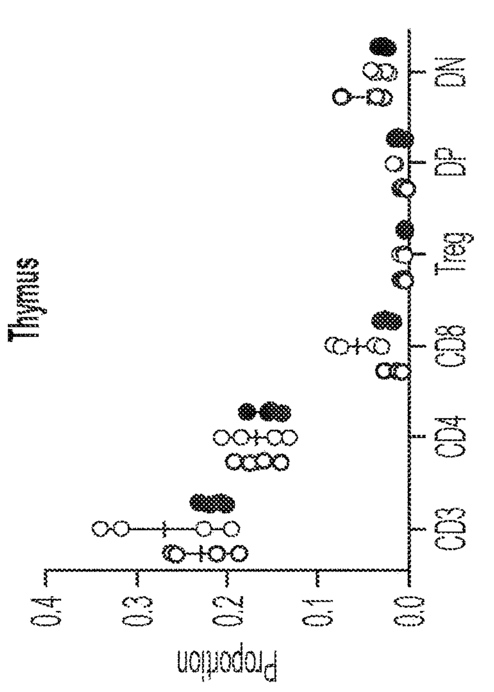
FIG. 12 shows NR-V04 does not influence T cell development in normal mice. Normal male mice were treated with 0.75 mg/kg celastrol or 1.8 mg/kg NR-V04, twice weekly for 3 weeks. Thymus (FIG. 12A) and spleen (FIG. 12B) were collected for T cell quantitation by flow cytometry.
Figure 12B:
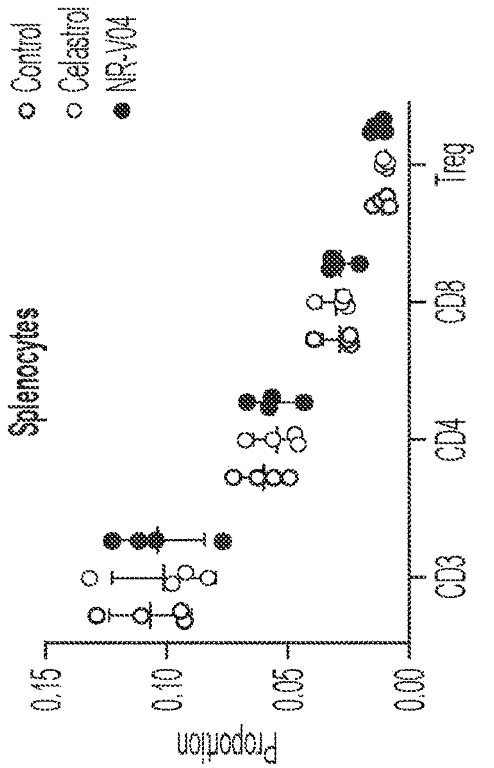
Figure 13A:
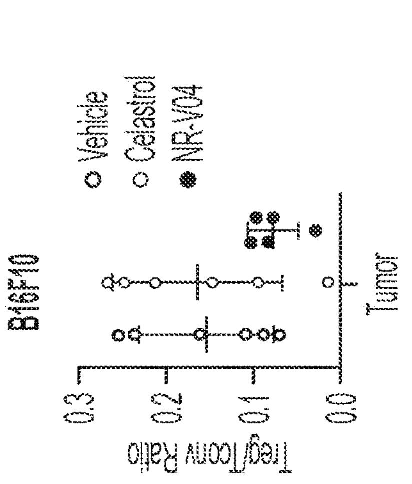
FIG. 13A-FIG. 13C. Influence of NR-V04 treatment on TI-Tregs from (FIG. 13A) B16F10 melanoma, 1.8 mg/kg twice weekly for 3 weeks.
Figure 13B:
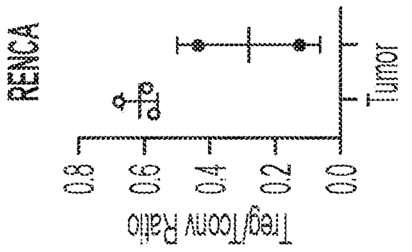
Figure 13C:
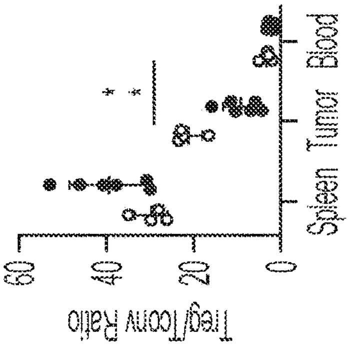
Figure 13D:
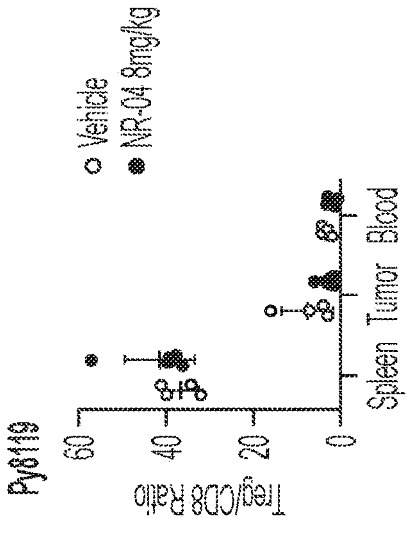

Mice bearing B16F10 melanoma were treated with the same molar amount of celastrol or NR-V04. NR-V04 significantly reduces tumor growth in C57BL/6J male mice (FIG. 10A-B), but the warhead celastrol has an opposite effect on tumor growth (FIG. 10A). The NR-V04-mediated tumor suppressing effect is dependent on intact immune system since this effect is diminished in NSG mice bearing B16F10 melanoma, suggestive of T, B or NK cell-mediated effect since NSG mice have no active T, B or NK cells (FIG. 10C). In addition, we found that NR-V04 has no significant toxicity as this dose regimen, with mice showing normal coat, behavior, posture and body weight (FIG. 11), but celastrol treatment leads to significant body weight change (FIG. 11). When normal mice were treated similarly for up to 3 weeks, NR-V04 did not influence the body weight and did not change the normal development of T cells as shown in thymus (FIG. 12A) and spleen (FIG. 12B).

NR-V04 Exhibits On-Target Immune Modulatory Effect to TI-Tregs and CD8+ T Cells.

Using multiparameter flow cytometry, we were able to quantitate the number of TI-Tregs from various tumor models, including B16F10 melanoma, RENCA renal cancer and Py8119 breast cancer models (FIG. 13A-13D, **: P<0.01 for Py8119 model).

Figure 14B:
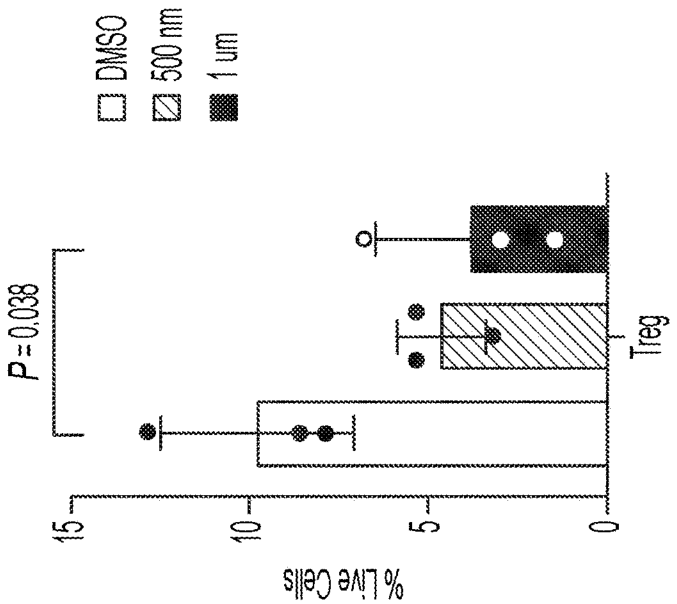
FIG. 14A-14B, different sub-population of T cell numbers were quantitated via flow cytometry (FIG. 14A), with Treg panel separated (FIG. 14B).
Figure 14A:
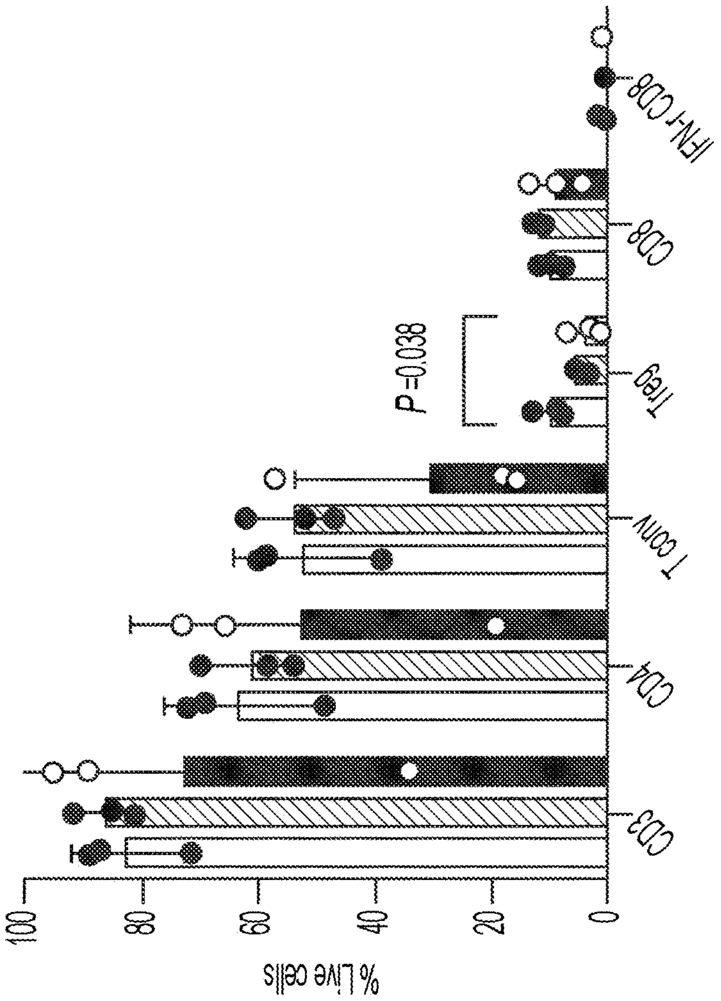

In agreement with the in vivo models, we also activated all human T cells from PBMC of cancer patients, following with the treatment of various concentrations of NR-V04. We found that NR-V04 has no impact on various T cell populations (FIG. 14A), but leads to selectively elimination of Tregs (FIG. 14B).

Figure 15A:
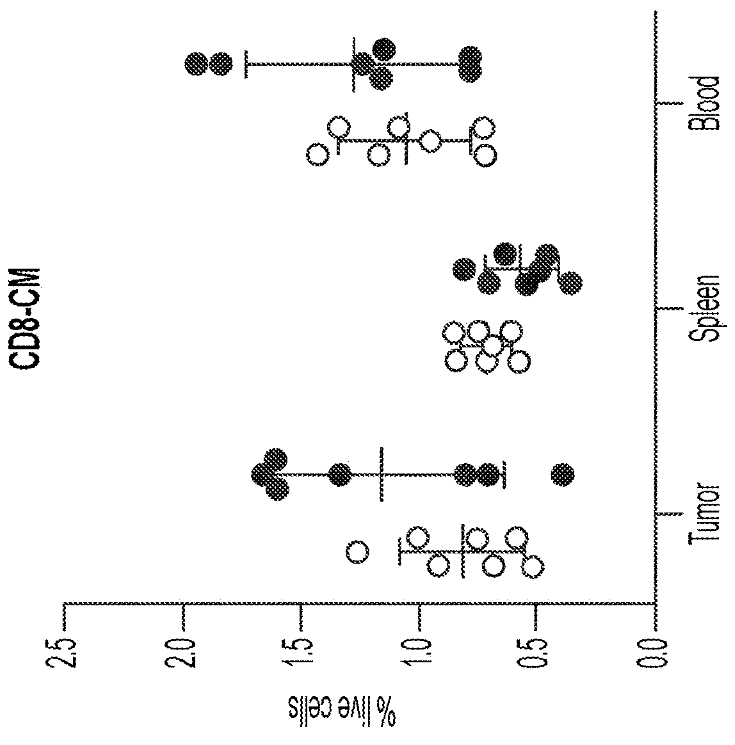
FIG. 15A. CD44+CD62L+(central memory, CM) and FIG. 15B. CD44+CD62L− (effector memory, EM) of CD8+ T cells were quantitated using flow cytometry.
Figure 15B:
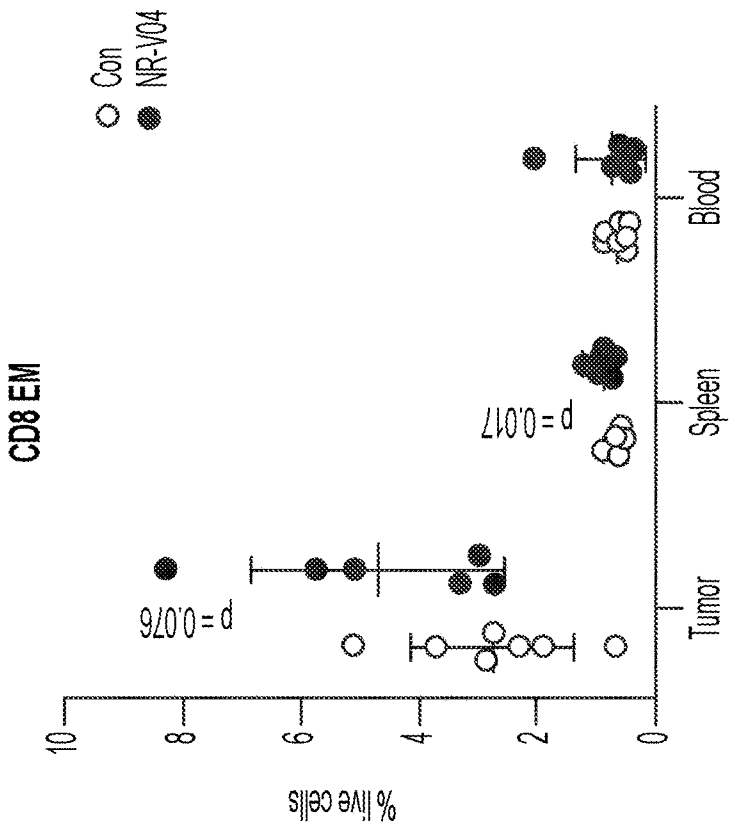
FIG. 15 shows NR-V04 treatment leads to increased CD8 T cell activation in various tumor models. B16F10 tumor bearing mice were treated with control vehicle or 1.8 mg/kg of NR-V04 for one week (two doses). CD8 T cells were analyzed for activation from tumors, spleen and blood.

We also determined the impact of NR-V04 on exhaustion and activation of $CD8^+$ T cells. We found NR-V04 treatment leads to significant increase of effector memory population of $CD8^+$ T cells, known to be the major tumor-fighting $CD8^+$ T cell population, but there is no significant change in central memory $CD8^+$ T cells (FIG. 15).

Figure 16:
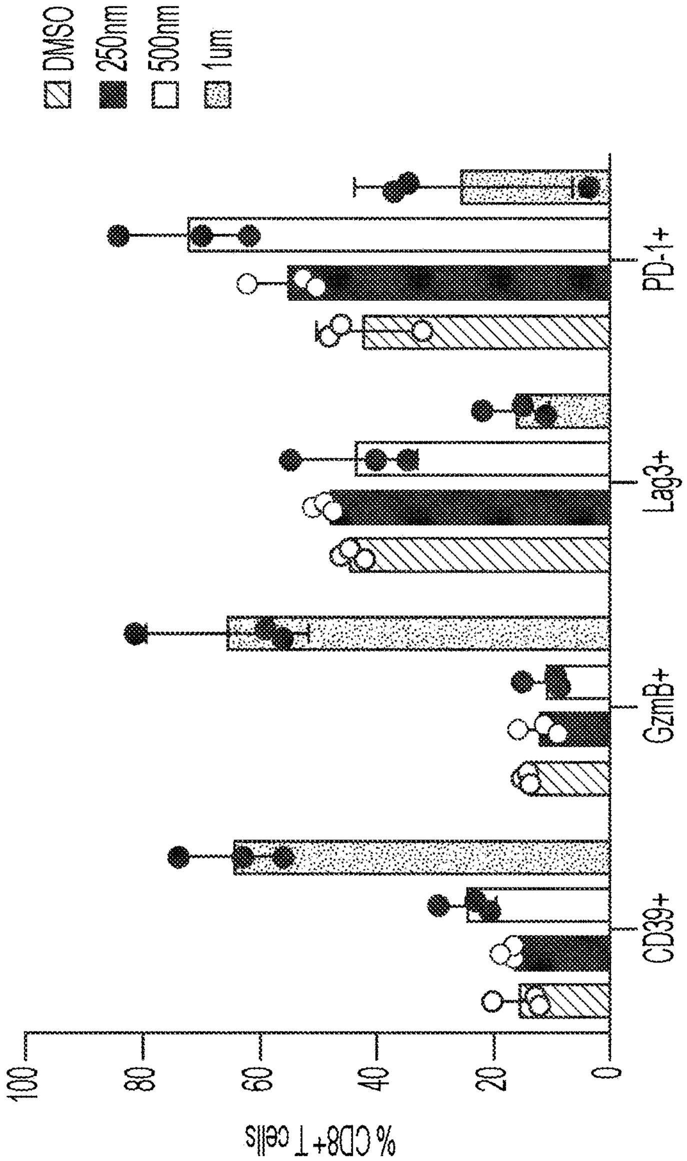
FIG. 16 shows NR-V04 treatment leads to increased CD8 T cell activation and reduced exhaustion. Splenic CD8+ T cells were purified from OT-1 transgenic mice, treated with 10 ng/ml of OVA peptides for 5 days, following with NR-V04 treatment at 250 nM, 500 nM or 1 μM. CD39+, granzyme B+($P<0.0001$), Lag3+ or PD-1+CD8 T cells ($P<0.05$) were quantitated using flow cytometry.

To induce antigen specific exhaustion of $CD8^+$ T cells, we purified $CD8^+$ T cells from OT-1 mice that expresses T cell receptor targeting OVA antigen. We treated these OT-1 CD8 T cells with OVA peptide for 5 days to induce their exhaustion, following with NR-V04 treatment with various concentrations. We found that 1 μM of NR-V04 treatment significantly reduced the percent of PD-$1^+$ or $Lag3^+$ exhausted CD8 T cells, but an increase in granzyme B+ active CD8 T cells (FIG. 16).

NR-V04 Exhibits Excellent Pharmacokinetics (PK).

Figure 17C:
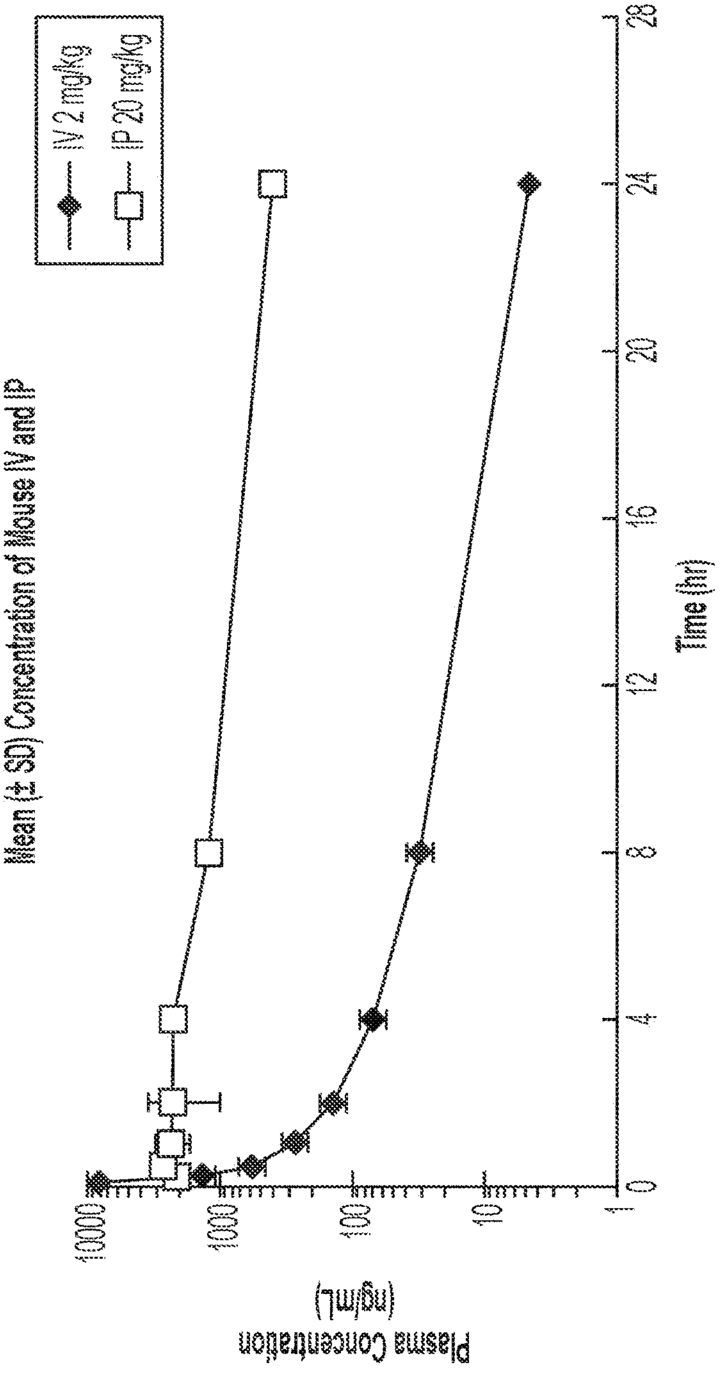
FIG. 17 shows the pharmacokinetics (PK) of NR-V04 in mouse. Plasma concentrations of NR-V04 were determined by LC/MS/MS (Instrument: AB Sciex 6500 (#15)) using service from BioDuro Inc, at different time points after mice receiving iv injection of 2 mg/kg or ip injection of 20 mg/kg. PK values for iv (2 mg/kg, FIG. 17A) or ip (20 mg/kg, FIG. 17B) are shown and summarized (FIG. 17C).

PK was determined for NR-V04 for iv. injection of 2 mg/kg or ip injection of 20 mg/kg (FIG. 17). NR-V04 has an average half-life of 5.36 hrs via iv injection (FIG. 17A, 17C) and 8.58 hrs via ip injection (FIG. 17B, 17C); the latter, showed 98% release rate into the plasma (F (%) in FIG. 17B).

Compound Preparation

General procedure: A mixture of the celastrol (1.0 equiv.), amine (1.0 equiv.), PyBOP (1.05 equiv.) and DIPEA (5.0 equiv.) in DMF was stirred at room temperature for 2 h.

The mixture was poured into water and extracted with ethyl acetate. The combined organic layers were washed with $NH_4Cl$ (aq.)×1, brine×1, dried over anhydrous $Na_2SO_4$, filtered, and concentrated under vacuum. The crude product was purified by flash column chromatography to afford the desired compound.

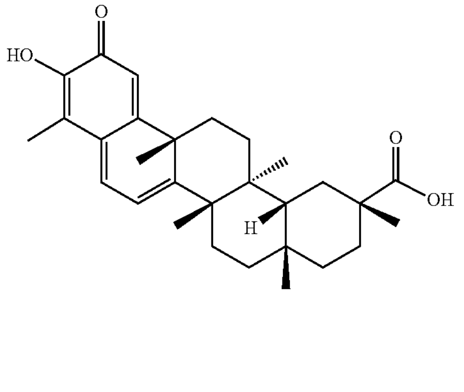

+

-continued
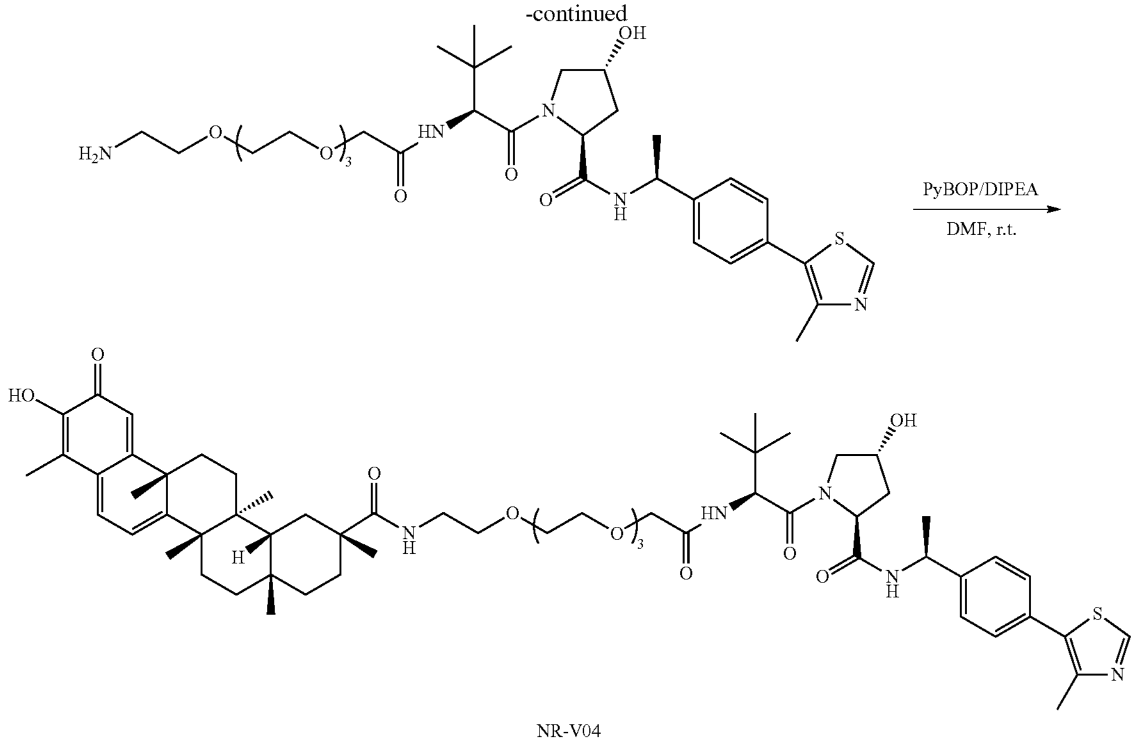
NR-V04
NR-V04 was obtained as red crystal (12 mg, yield 55%). $^{1}H$ NMR (600 MHz, $CDCl_3$) δ 8.68 (s, 1H), 7.44-7.31 (m, 5H), 7.23-7.04 (m, 3H), 6.60-6.52 (m, 2H), 6.37 (d, J=7.3 Hz, 1H), 5.14-5.04 (m, 1H), 4.70-4.62 (m, 1H), 4.59 (d, J=8.9 Hz, 1H), 4.53-4.46 (m, 1H), 4.07 (s, 2H), 3.97-3.89 (m, 1H), 3.77-3.46 (m, 16H), 3.20 (s, 1H), 2.60-2.28 (m, 7H), 2.23-2.09 (m, 5H), 2.06-1.78 (m, 6H), 1.70-1.39 (m, 14H), 1.18-1.09 (m, 6H), 1.07-0.84 (m, 10H), 0.58 (s, 3H). ESI $[M+H]^+$=1110.6.
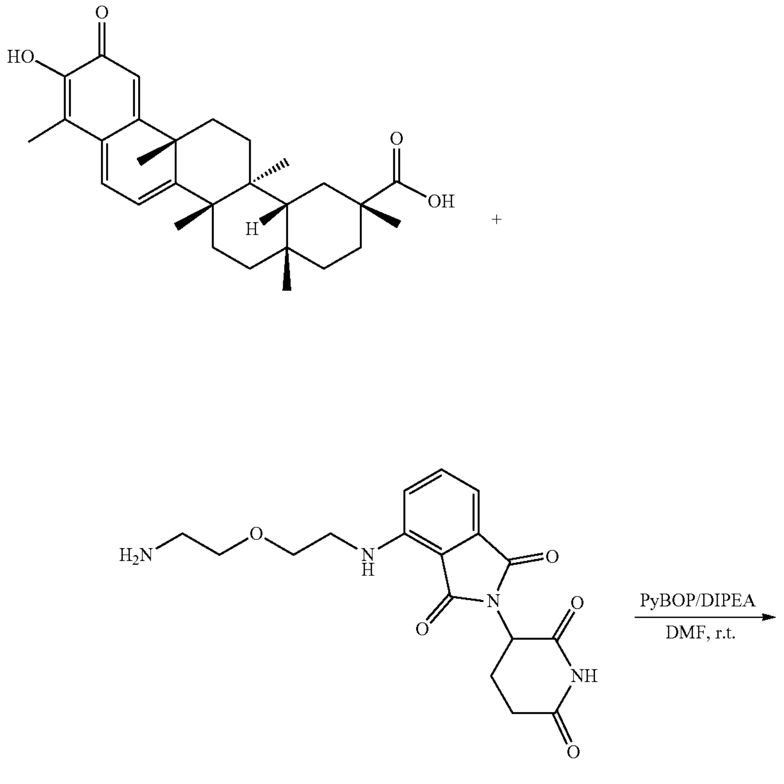

-continued

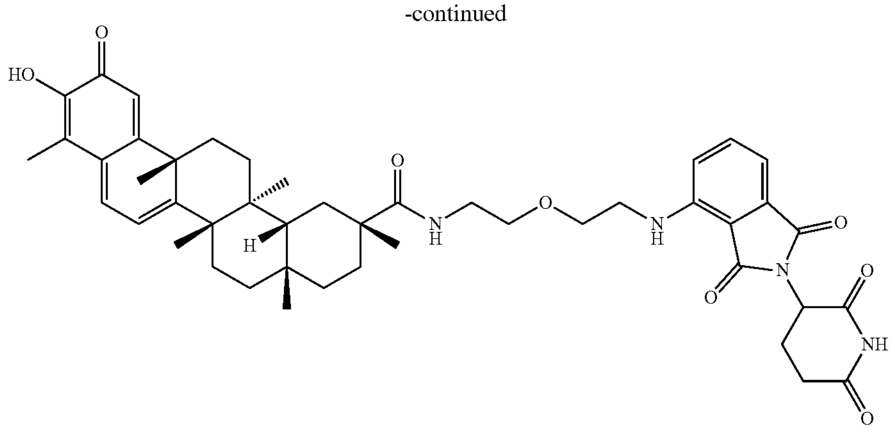

NR-C91

NR-C91 was obtained as orange crystal (9 mg, yield 51%). $^{1}H$ NMR (600 MHz, $CDCl_3$) δ 8.39 (d, J=11.1 Hz, 1H), 7.59-7.50 (m, 1H), 7.16 (d, J=7.1 Hz, 1H), 7.06-6.99 (m, 2H), 6.97 (d, J=8.5 Hz, 1H), 6.56 (t, J=5.5 Hz, 1H), 6.53-6.48 (m, 1H), 6.32 (dd, J=7.2, 4.0 Hz, 1H), 6.25-6.16 (m, 1H), 4.99-4.92 (m, 1H), 3.67 (t, J=5.1 Hz, 2H), 3.56-3.44 (m, 4H), 3.42-3.32 (m, 2H), 2.95-2.73 (m, 3H), 2.37 (dd, J=15.7, 6.8 Hz, 1H), 2.22 (s, 3H), 2.19-1.98 (m, 4H), 1.92-1.76 (m, 3H), 1.66-1.40 (m, 10H), 1.24 (s, 3H), 1.13 (d, J=3.5 Hz, 3H), 1.10 (s, 3H), 0.99-0.92 (m, 1H), 0.63 (s, 3H). ESI $[M+H]^+$=793.4.

Additional Compound:

Compound NR-C34 has the structure;

NR-C34

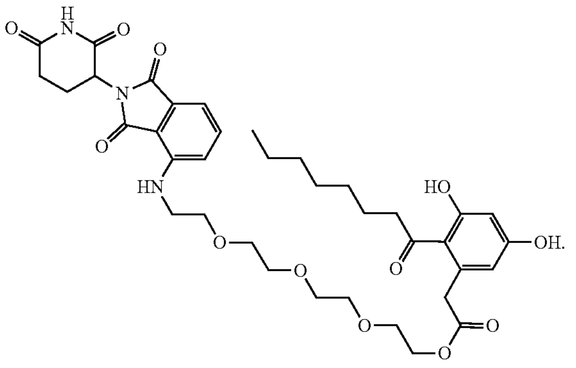

REFERENCES CITED

1. Wenzl K, Troppan K, Neumeister P, Deutsch A J. The nuclear orphan receptor NR4A1 and NR4A3 as tumor suppressors in hematologic neoplasms. Curr Drug Targets. 2015; 16(1):38-46. Epub 2014/11/21. doi: 10.2174/1389450115666141120112818. PubMed PMID: 25410408.
2. Mullican S E, Zhang S, Konopleva M, Ruvolo V, Andreeff M, Milbrandt J, Conneely O M. Abrogation of nuclear receptors Nr4a3 and Nr4a1 leads to development of acute myeloid leukemia. Nat Med. 2007; 13(6):730-5. Epub 2007/05/23. doi: 10.1038/nm1579. PubMed PMID: 17515897.
3. Deutsch A J, Rinner B, Wenzl K, Pichler M, Troppan K, Steinbauer E, Schwarzenbacher D, Reitter S, Feichtinger J, Tierling S, Prokesch A, Scheideler M, Krogsdam A, Thallinger G G, Schaider H, Beham-Schmid C, Neumeister P. NR4A1-mediated apoptosis suppresses lymphomagenesis and is associated with a favorable cancer-specific survival in patients with aggressive B-cell lymphomas. Blood. 2014; 123(15):2367-77. Epub 2014/02/21. doi: 10.1182/blood-2013-08-518878. PubMed PMID: 24553175.
4. Hedrick E, Lee S O, Doddapaneni R, Singh M, Safe S. Nuclear receptor 4A1 as a drug target for breast cancer chemotherapy. Endocr Relat Cancer. 2015; 22(5):831-40. Epub 2015/08/01. doi: 10.1530/ERC-15-0063. PubMed PMID: 26229035.
5. Hedrick E, Li X, Cheng Y, Lacey A, Mohankumar K, Zarei M, Safe S. Potent inhibition of breast cancer by bis-indole-derived nuclear receptor 4A1 (NR4A1) antagonists. Breast cancer research and treatment. 2019; 177(1):29-40. Epub 2019/05/24. doi: 10.1007/s10549-019-05279-9. PubMed PMID: 31119568; PMCID: PMC6681651.
6. Hedrick E, Safe S. Transforming Growth Factor beta/NR4A1-Inducible Breast Cancer Cell Migration and Epithelial-to-Mesenchymal Transition Is p38alpha (Mitogen-Activated Protein Kinase 14) Dependent. Mol Cell Biol. 2017; 37(18). Epub 2017/07/05. doi: 10.1128/MCB.00306-17. PubMed PMID: 28674186; PMCID: PMC5574050.
7. Hedrick E, Lee S O, Doddapaneni R, Singh M, Safe S. NR4A1 Antagonists Inhibit beta1-Integrin-Dependent Breast Cancer Cell Migration. Mol Cell Biol. 2016; 36(9):1383-94. Epub 2016/03/02. doi: 10.1128/MCB.00912-15. PubMed PMID: 26929200; PMCID: PMC4836213.
8. Liu X, Wang Y, Lu H, Li J, Yan X, Xiao M, Hao J, Alekseev A, Khong H, Chen T, Huang R, Wu J, Zhao Q, Wu Q, Xu S, Wang X, Jin W, Yu S, Wang Y, Wei L, Wang A, Zhong B, Ni L, Liu X, Nurieva R, Ye L, Tian Q, Bian X W, Dong C. Genome-wide analysis identifies NR4A1 as a key mediator of T cell dysfunction. Nature. 2019; 567(7749):525-9. Epub 2019/03/01. doi: 10.1038/s41586-019-0979-8. PubMed PMID: 30814730; PMCID: PMC6507425.
9. Chen J, Lopez-Moyado I F, Seo H, Lio C J, Hempleman L J, Sekiya T, Yoshimura A, Scott-Browne J P, Rao A. NR4A transcription factors limit CAR T cell function in solid tumours. Nature. 2019; 567(7749):530-4. Epub 2019/03/01. doi: 10.1038/s41586-019-0985-x. PubMed PMID: 30814732; PMCID: PMC6546093.

10. Karki K, Wright G A, Mohankumar K, Jin U H, Zhang X H, Safe S. A Bis-Indole-Derived NR4A1 Antagonist Induces PD-L1 Degradation and Enhances Anti-Tumor Immunity. Cancer Res. 2020. Epub 2020/01/09. doi: 10.1158/0008-5472.CAN-19-2314. PubMed PMID: 31911554.

11. Muscat G E, Eriksson N A, Byth K, Loi S, Graham D, Jindal S, Davis M J, Clyne C, Funder J W, Simpson E R, Ragan M A, Kuczek E, Fuller P J, Tilley W D, Leedman P J, Clarke C L. Research resource: nuclear receptors as transcriptome: discriminant and prognostic value in breast cancer. Mol Endocrinol. 2013; 27(2):350-65. Epub 2013/01/08. doi: 10.1210/me.2012-1265. PubMed PMID: 23292282; PMCID: PMC5417325.

12. Zhou F, Drabsch Y, Dekker T J, de Vinuesa A G, Li Y, Hawinkels L J, Sheppard K A, Goumans M J, Luwor R B, de Vries C J, Mesker W E, Tollenaar R A, Devilee P, Lu CX, Zhu H, Zhang L, Dijke P T. Nuclear receptor NR4A1 promotes breast cancer invasion and metastasis by activating TGF-beta signalling. Nature communications. 2014; 5:3388. Epub 2014/03/04. doi: 10.1038/ncomms4388. PubMed PMID: 24584437.

13. Hedrick E, Lee S O, Kim G, Abdelrahim M, Jin U H, Safe S, Abudayyeh A. Nuclear Receptor 4A1 (NR4A1) as a Drug Target for Renal Cell Adenocarcinoma. PloS one. 2015; 10(6):e0128308. Epub 2015/06/04. doi: 10.1371/journal.pone.0128308. PubMed PMID: 26035713; PMCID: PMC4452731.

14. Mohankumar K, Li X, Sridharan S, Karki K, Safe S. Nuclear receptor 4A1 (NR4A1) antagonists induce ROS-dependent inhibition of mTOR signaling in endometrial cancer. Gynecol Oncol. 2019; 154(1):218-27. Epub 2019/05/06. doi: 10.1016/j.ygyno.2019.04.678. PubMed PMID: 31053403; PMCID: PMC6625344.

15. Li X X, Wang Z J, Zheng Y, Guan Y F, Yang P B, Chen X, Peng C, He J P, Ai Y L, Wu S F, Chien K Y, Wu Q, Chen H Z. Nuclear Receptor Nur77 Facilitates Melanoma Cell Survival under Metabolic Stress by Protecting Fatty Acid Oxidation. Mol Cell. 2018; 69(3):480-92 e7. Epub 2018/02/06. doi: 10.1016/j.molcel.2018.01.001. PubMed PMID: 29395065.

16. Hazel T G, Nathans D, Lau L F. A gene inducible by serum growth factors encodes a member of the steroid and thyroid hormone receptor superfamily. Proceedings of the National Academy of Sciences of the United States of America. 1988; 85(22):8444-8. Epub 1988/11/01. doi: 10.1073/pnas.85.22.8444. PubMed PMID: 3186734; PMCID: PMC282474.

17. Milbrandt J. Nerve growth factor induces a gene homologous to the glucocorticoid receptor gene. Neuron. 1988; 1(3):183-8. Epub 1988/05/01. doi: 10.1016/0896-6273(88)90138-9. PubMed PMID: 3272167.

18. Liu Z G, Smith S W, McLaughlin K A, Schwartz L M, Osborne B A. Apoptotic signals delivered through the T-cell receptor of a T-cell hybrid require the immediate-early gene nur77. Nature. 1994; 367(6460):281-4. Epub 1994/01/20. doi: 10.1038/367281a0. PubMed PMID: 8121494.

19. Woronicz J D, Calnan B, Ngo V, Winoto A. Requirement for the orphan steroid receptor Nur77 in apoptosis of T-cell hybridomas. Nature. 1994; 367(6460):277-81. Epub 1994/01/20. doi: 10.1038/367277a0. PubMed PMID: 8121493.

20. Fassett M S, Jiang W, D'Alise A M, Mathis D, Benoist C. Nuclear receptor Nr4a1 modulates both regulatory T-cell (Treg) differentiation and clonal deletion. Proceedings of the National Academy of Sciences of the United States of America. 2012; 109(10):3891-6. Epub 2012/02/22. doi: 10.1073/pnas.1200090109. PubMed PMID: 22345564; PMCID: PMC3309794.

21. Hibino S, Chikuma S, Kondo T, I to M, Nakatsukasa H, Omata-Mise S, Yoshimura A. Inhibition of Nr4a Receptors Enhances Antitumor Immunity by Breaking Treg-Mediated Immune Tolerance. Cancer Res. 2018; 78(11):3027-40. Epub 2018/03/22. doi: 10.1158/0008-5472.CAN-17-3102. PubMed PMID: 29559474.

22. Khan S, Zhang X, Lv D, Zhang Q, He Y, Zhang P, Liu X, Thummuri D, Yuan Y, Wiegand J S, Pei J, Zhang W, Sharma A, McCurdy C R, Kuruvilla V M, Baran N, Ferrando A A, Kim Y M, Rogojina A, Houghton P J, Huang G, Hromas R, Konopleva M, Zheng G, Zhou D. A selective BCL-XL PROTAC degrader achieves safe and potent antitumor activity. Nat Med. 2019; 25(12):1938-47. Epub 2019/12/04. doi: 10.1038/s41591-019-0668-z. PubMed PMID: 31792461.

23. Schapira M, Calabrese M F, Bullock A N, Crews C M. Targeted protein degradation: expanding the toolbox. Nat Rev Drug Discov. 2019; 18(12):949-63. Epub 2019/10/30. doi: 10.1038/s41573-019-0047-y. PubMed PMID: 31666732.

24. Neklesa T K, Winkler J D, Crews C M. Targeted protein degradation by PROTACs. Pharmacol Ther. 2017; 174:138-44. Epub 2017/02/14. doi: 10.1016/j.pharmthera.2017.02.027. PubMed PMID: 28223226.

25. Wu L, Chen L. Characteristics of Nur77 and its ligands as potential anticancer compounds (Review). Mol Med Rep. 2018; 18(6):4793-801. Epub 2018/10/03. doi: 10.3892/mmr.2018.9515. PubMed PMID: 30272297; PMCID: PMC6236262.

26. Zhan Y, Du X, Chen H, Liu J, Zhao B, Huang D, Li G, Xu Q, Zhang M, Weimer B C, Chen D, Cheng Z, Zhang L, Li Q, Li S, Zheng Z, Song S, Huang Y, Ye Z, Su W, Lin S C, Shen Y, Wu Q. Cytosporone B is an agonist for nuclear orphan receptor Nur77. Nat Chem Biol. 2008; 4(9):548-56. Epub 2008/08/12. doi: 10.1038/nchembio.106. PubMed PMID: 18690216.

27. Liu J J, Zeng H N, Zhang L R, Zhan Y Y, Chen Y, Wang Y, Wang J, Xiang S H, Liu W J, Wang W J, Chen H Z, Shen Y M, Su W J, Huang P Q, Zhang H K, Wu Q. A unique pharmacophore for activation of the nuclear orphan receptor Nur77 in vivo and in vitro. Cancer Res. 2010; 70(9):3628-37. Epub 2010/04/15. doi: 10.1158/0008-5472.CAN-09-3160. PubMed PMID: 20388790.

28. Hu M, Luo Q, Alitongbieke G, Chong S, Xu C, Xie L, Chen X, Zhang D, Zhou Y, Wang Z, Ye X, Cai L, Zhang F, Chen H, Jiang F, Fang H, Yang S, Liu J, Diaz-Meco M T, Su Y, Zhou H, Moscat J, Lin X, Zhang X K. Celastrol-Induced Nur77 Interaction with TRAF2 Alleviates Inflammation by Promoting Mitochondrial Ubiquitination and Autophagy. Mol Cell. 2017; 66(1):141-53 e6. Epub 2017/04/08. doi: 10.1016/j.molcel.2017.03.008. PubMed PMID: 28388439; PMCID: PMC5761061.

29. Chen Z, Zhang D, Yan S, Hu C, Huang Z, Li Z, Peng S, Li X, Zhu Y, Yu H, Lian B, Kang Q, Li M, Zeng Z, Zhang X K, Su Y. SAR study of celastrol analogs targeting Nur77-mediated inflammatory pathway. Eur J Med Chem. 2019; 177:171-87. Epub 2019/05/28. doi: 10.1016/j.ejmech.2019.05.009. PubMed PMID: 31132532.

30. Narayan P, Wahby S, Gao J J, Amiri-Kordestani L, Ibrahim A, Bloomquist E, Tang S, Xu Y, Liu J, Fu W, Song P, King-Kallimanis B L, Hou S, Gong Y, Kalavar S, Ghosh S, Philip R, Goldberg K B, Theoret M R, Blumenthal G M, Kluetz P G, Sridhara R, Pazdur R, Beaver J A. FDA Approval Summary: Atezolizumab plus paclitaxel protein-bound for the treatment of patients with advanced or metastatic TNBC whose tumors express PD-L1. Clinical cancer research: an official journal of the American Association for Cancer Research. 2020. Epub 2020/02/01. doi: 10.1158/1078-0432.CCR-19-3545. PubMed PMID: 32001481.

31. Plitas G, Konopacki C, Wu K, Bos P D, Morrow M, Putintseva E V, Chudakov D M, Rudensky A Y. Regulatory T Cells Exhibit Distinct Features in Human Breast Cancer. Immunity. 2016; 45(5):1122-34. Epub 2016/11/17. doi: 10.1016/j.immuni.2016.10.032. PubMed PMID: 27851913; PMCID: PMC5134901.

32. Borcherding N, Ahmed K, Voigt A P, Vishwakarma A, Kolb R, Kluz P, Pandey G, Gibson-Corley K N, Klesney-Tait J, Zhu Y, Lu J, Lu J, Huang X, Cheng J, Zheng S G, Wu X, Zakharia Y, Zhang W. Transcriptional heterogeneity in cancer-associated regulatory T cells is predictive of survival. BioRxiv: Cold Spring Harbor Laboratory; 2018.

33. Vishwakarma A, Bocherding N, Chimenti M S, Vishwakarma P, Nepple K, Salem A, Jenkins R W, Zhang W, Zakharia Y. Mapping the Immune Landscape of Clear Cell Renal Cell Carcinoma by Single-Cell RNA-seq. Cold Spring Harbor Laboratory; 2019.

34. Zheng C, Zheng L, Yoo J K, Guo H, Zhang Y, Guo X, Kang B, Hu R, Huang J Y, Zhang Q, Liu Z, Dong M, Hu X, Ouyang W, Peng J, Zhang Z. Landscape of Infiltrating T Cells in Liver Cancer Revealed by Single-Cell Sequencing. Cell. 2017; 169(7):1342-56.e16. doi: 10.1016/j.cell.2017.05.035. PubMed PMID: 28622514.

35. Sekiya T, Hibino S, Saeki K, Kanamori M, Takaki S, Yoshimura A. Nr4a Receptors Regulate Development and Death of Labile Treg Precursors to Prevent Generation of Pathogenic Self-Reactive Cells. Cell Rep. 2018; 24(6): 1627-38 e6. Epub 2018/08/09. doi: 10.1016/j.celrep.2018.07.008. PubMed PMID: 30089271.

36. Goodson L H, Barvick L, Stone R G, Ibach M, Palmer J. Inhibition screening data using sarcoma 180 and adenocarcinoma E0771. Cancer Res. 1955; Suppl. 2:81-102. Epub 1955/01/01. PubMed PMID: 14379183.

37. Kolb R, Phan L, Borcherding N, Liu Y, Yuan F, Janowski A M, Xie Q, Markan K R, Li W, Potthoff M J, Fuentes-Mattei E, Ellies L G, Knudson C M, Lee M H, Yeung S J, Cassel S L, Sutterwala F S, Zhang W. Obesity-associated NLRC4 inflammasome activation drives breast cancer progression. Nature communications. 2016; 7:13007. Epub 2016/10/07. doi: 10.1038/ncomms13007. PubMed PMID: 27708283; PMCID: PMC5059727.

38. Ewens A, Mihich E, Ehrke M J. Distant metastasis from subcutaneously grown E0771 medullary breast adenocarcinoma. Anticancer Res. 2005; 25(6B):3905-15. Epub 2005/11/30. PubMed PMID: 16312045.

39. Biswas T, Gu X, Yang J, Ellies L G, Sun L Z. Attenuation of TGF-β signaling supports tumor progression of a mesenchymal-like mammary tumor cell line in a syngeneic murine model. Cancer Lett. 2014; 346(1):129-38. Epub 2013/12/22. doi: 10.1016/j.canlet.2013.12.018. PubMed PMID: 24368187; PMCID: PMC3947668.

40. Kolb R, Kluz P, Tan Z W, Borcherding N, Bormann N, Vishwakarma A, Balcziak L, Zhu P, Davies B S, Gourronc F, Liu L Z, Ge X, Jiang B H, Gibson-Corley K, Klingelhutz A, Tan N S, Zhu Y, Sutterwala F S, Shen X, Zhang W. Obesity-associated inflammation promotes angiogenesis and breast cancer via angiopoietin-like 4. Oncogene. 2019; 38(13):2351-63. Epub 2018/12/05. doi: 10.1038/s41388-018-0592-6. PubMed PMID: 30518876; PMCID: PMC6440811.

41. Aslakson C J, Miller F R. Selective events in the metastatic process defined by analysis of the sequential dissemination of subpopulations of a mouse mammary tumor. Cancer Res. 1992; 52(6):1399-405. PubMed PMID: 1540948.

42. Pulaski B A, Terman D S, Khan S, Muller E, Ostrand-Rosenberg S. Cooperativity of *Staphylococcal aureus* enterotoxin B superantigen, major histocompatibility complex class II, and CD80 for immunotherapy of advanced spontaneous metastases in a clinically relevant postoperative mouse breast cancer model. Cancer Res. 2000; 60(10):2710-5.

PubMed PMID: 10825145.

43. Tan W, Zhang W, Strasner A, Grivennikov S, Cheng J Q, Hoffman R M, Karin M. Tumour-infiltrating regulatory T cells stimulate mammary cancer metastasis through RANKL-RANK signalling. Nature. 2011; 470(7335): 548-53. Epub 2011/02/18. doi: 10.1038/nature09707. PubMed PMID: 21326202; PMCID: PMC3166217.

44. Zhang W, Tan W, Wu X, Poustovoitov M, Strasner A, Li W, Borcherding N, Ghassemian M, Karin M. A NIK-IKKalpha module expands ErbB2-induced tumor-initiating cells by stimulating nuclear export of p27/Kip1. Cancer cell. 2013; 23(5):647-59. doi: 10.1016/j.ccr.2013.03.012. PubMed PMID: 23602409; PMCID: 3981467.

45. Borcherding N, Vishwakarma A, Voigt A P, Bellizzi A, Kaplan J, Nepple K, Salem A K, Jenkins R W, Zakharia Y, Zhang W. Mapping the immune environment in clear cell renal carcinoma by single-cell genomics. Commun Biol. 2021; 4(1):122. Epub 2021/01/29. doi: 10.1038/s42003-020-01625-6. PubMed PMID: 33504936; PMCID: PMC7840906.

INCORPORATION BY REFERENCE

The contents of all references (including literature references, issued patents, published patent applications, and co-pending patent applications) cited throughout this application are hereby expressly incorporated herein in their entireties by reference.

EMBODIMENTS

Embodiment 1. A compound of Formula (I), or a pharmaceutically acceptable salt thereof:

Formula (I)

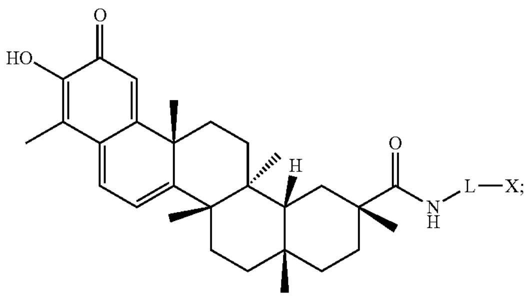

wherein L is $C_{4-8}$ alkylene or $C_{4-9}$ heteroalkylene, wherein $C_{4-9}$ heteroalkylene comprises 1-4 oxygen atoms; and X is

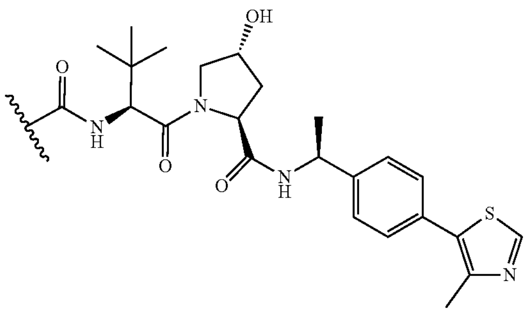

or

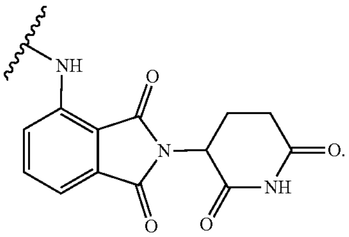 [SMILES: *Nc1cccc2c1C(=O)N(C1CCC(=O)NC1=O)C2=O]

Embodiment 2. The compound of embodiment 1, wherein X is

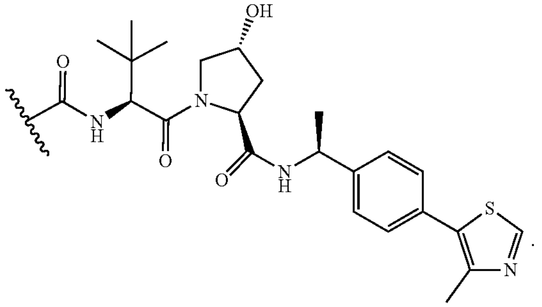 [SMILES: *C(=O)N[C@H](C(=O)N1C[C@H](O)C[C@H]1C(=O)N[C@@H](C)c1ccc(-c2scnc2C)cc1)C(C)(C)C]

Embodiment 3. The compound of embodiment 1, wherein X is

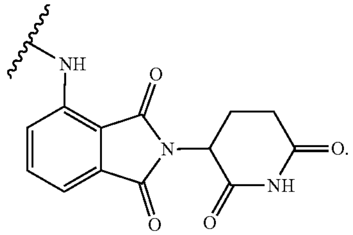

Embodiment 4. The compound of any of the preceding embodiments, wherein L is $C_{4-8}$ alkylene.

Embodiment 5. The compound of any of the preceding embodiments, wherein L is $C_{4-9}$ heteroalkylene comprising 1-4 oxygen atoms.

Embodiment 6. The compound of any of the preceding embodiments, wherein the compound has the formula:

NR-V03

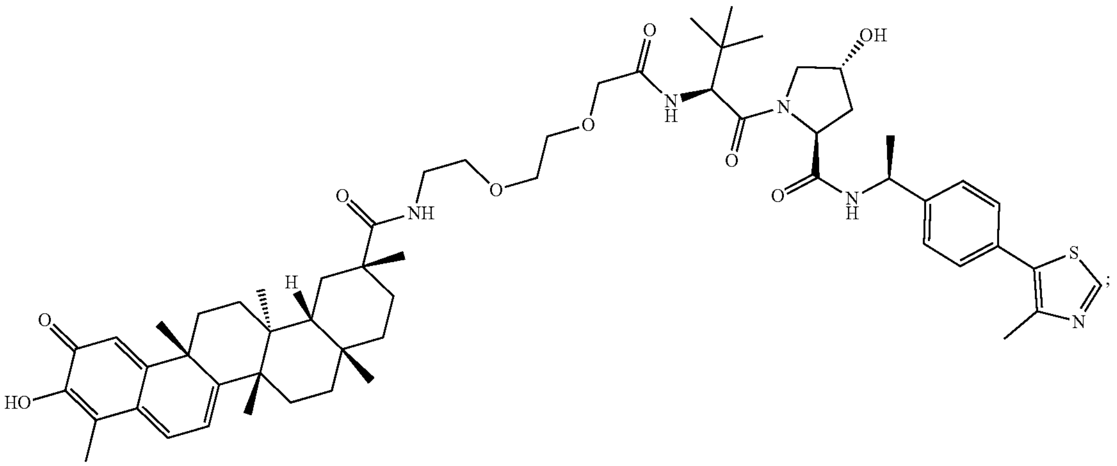

;

-continued
NR-V07
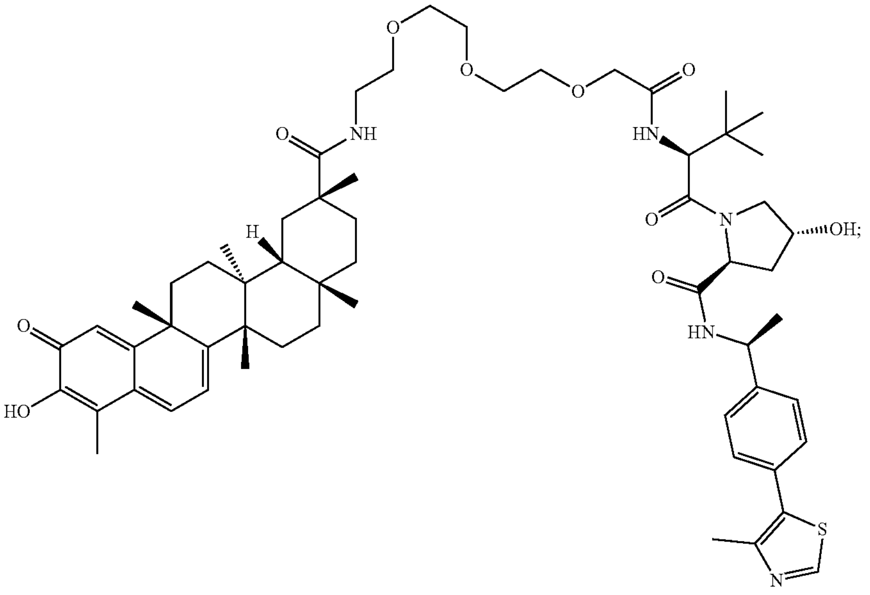
NR-V04
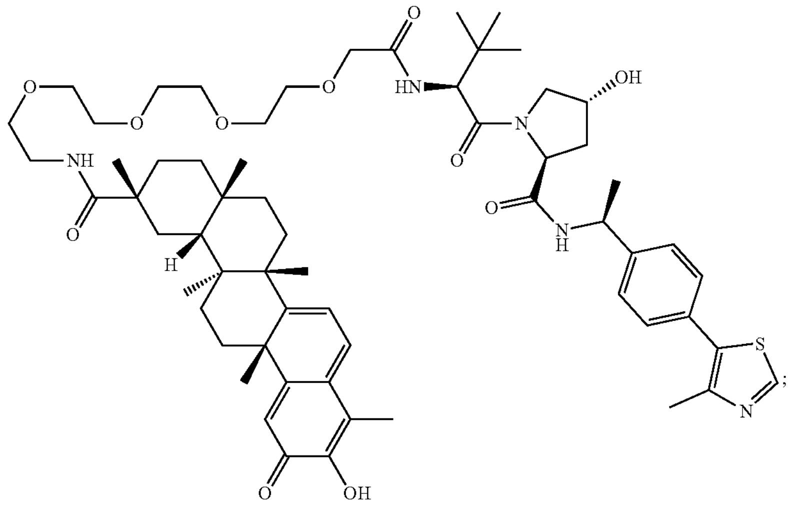
NR-V46
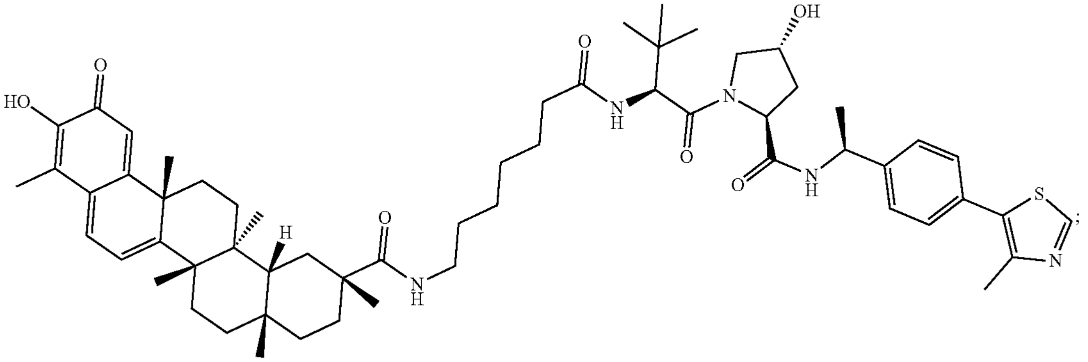

-continued
NR-V50
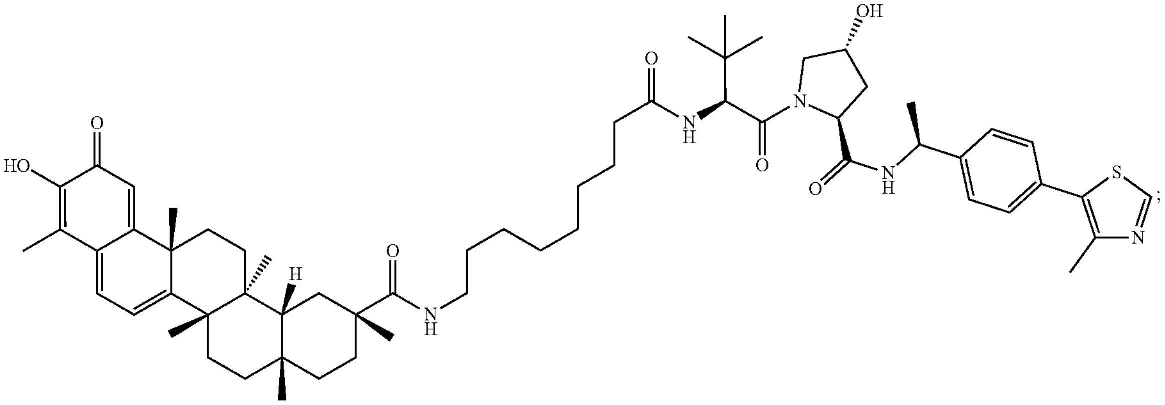
NR-C58
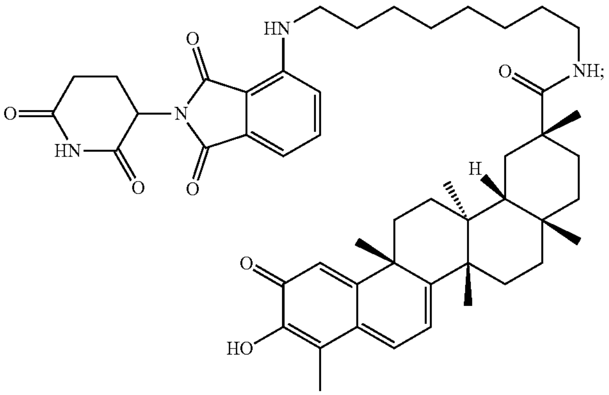
NR-C91
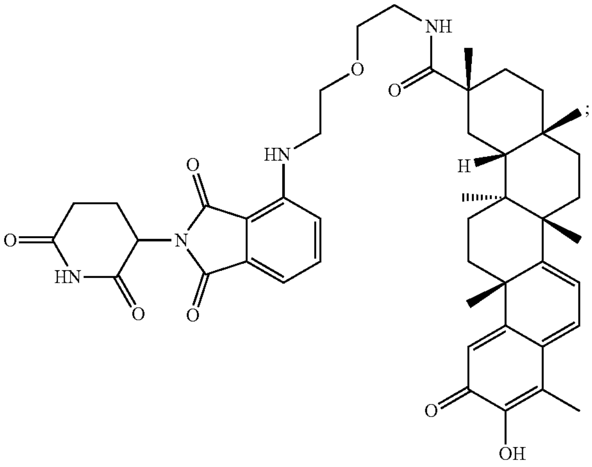

-continued

NR-C92

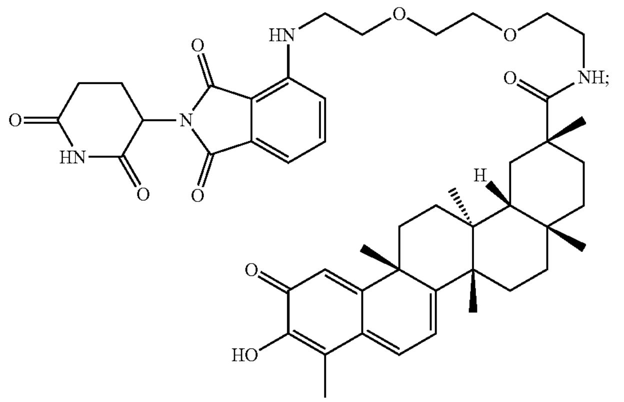

; or

NR-C93

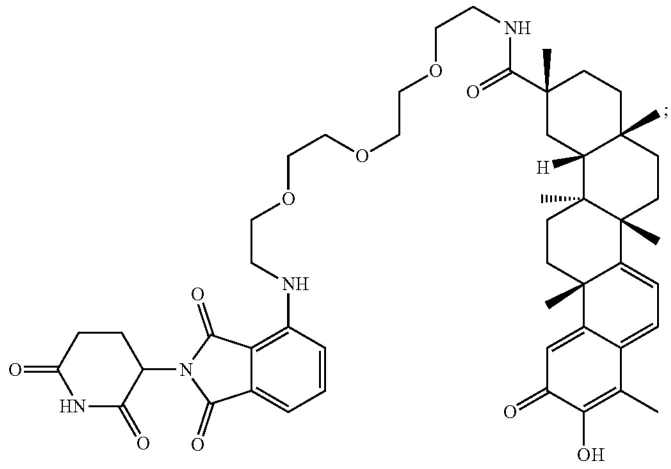

;

or a pharmaceutically acceptable salt thereof.

Embodiment 7. The compound of any of the preceding embodiments that is NR-V04, or a pharmaceutically acceptable salt thereof.

Embodiment 8. The compound of any of the preceding embodiments that is NR-C91, or a pharmaceutically acceptable salt thereof.

Embodiment 9. A pharmaceutical composition comprising a compound of any of the preceding embodiments, or a pharmaceutically acceptable salt thereof, and a pharmaceutically acceptable adjuvant.

Embodiment 10. The pharmaceutical composition of embodiment 9, further comprising an additional anti-cancer agent.

Embodiment 11. A method of treating cancer in a subject, comprising administration of a compound of any of the preceding embodiments, or a pharmaceutically acceptable salt thereof, or a pharmaceutical composition of any of the preceding embodiments, to the subject.

Embodiment 12. A method of treating cancer in a subject identified as in need thereof, comprising administration of a compound of any of the preceding embodiments, or a pharmaceutically acceptable salt thereof, or a pharmaceutical composition of any of the preceding embodiments, to the subject.

Embodiment 13. The method of embodiment 11 or 12, wherein the cancer is breast cancer, lung cancer, liver cancer, pancreatic cancer, intestinal cancer, cancer of the spleen, colon cancer, melanoma, solid tumor, thyroid carcinoma, esophageal adenocarcinomas, or bladder cancer.

Embodiment 14. The method of any of embodiments 11-13, wherein the cancer is breast cancer, lung cancer, thyroid carcinoma, esophageal adenocarcinomas, or bladder cancer.

Embodiment 15. The method of any of embodiments 11-14, further comprising administration of an additional anti-cancer agent.

Embodiment 16. A method of modulating Nuclear Receptor Subfamily 4 Group A Member 1 (NR4A1) in a subject, comprising administration of a compound of any of the preceding embodiments, or a pharmaceutically acceptable salt thereof, or a pharmaceutical composition of any of the preceding embodiments, to the subject.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed is:

1. A compound of Formula (I), or a pharmaceutically acceptable salt thereof:

Formula (I)

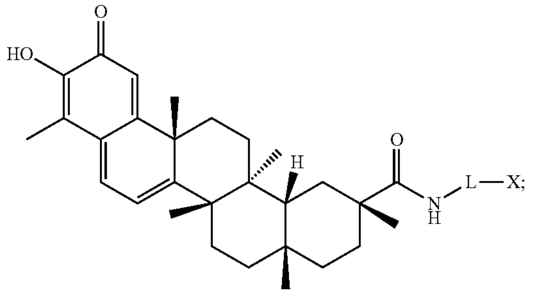

wherein L is $C_{4-8}$ alkylene or $C_{4-9}$ heteroalkylene, wherein the heteroatoms in $C_{4-9}$ heteroalkylene are 1-4 oxygen atoms; and X is

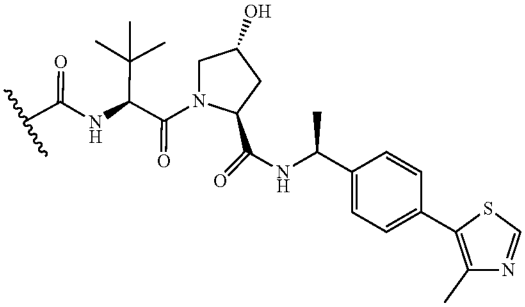

or

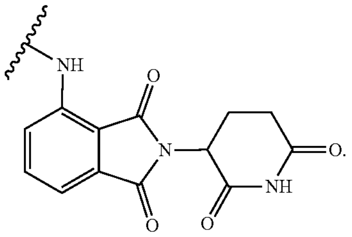 [SMILES: *Nc1cccc2c1C(=O)N(C1CCC(=O)NC1=O)C2=O]

2. The compound of claim 1, or a pharmaceutically acceptable salt thereof, wherein X is

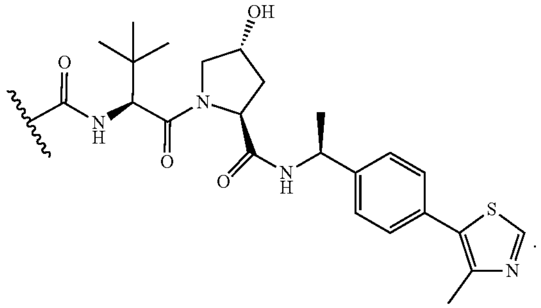 [SMILES: *C(=O)N[C@H](C(=O)N1C[C@H](O)C[C@H]1C(=O)N[C@@H](C)c1ccc(-c2scnc2C)cc1)C(C)(C)C]

3. The compound of claim 1, or a pharmaceutically acceptable salt thereof, wherein X is

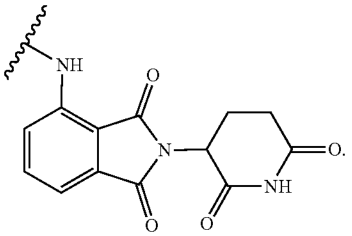 [SMILES: *Nc1cccc2c1C(=O)N(C1CCC(=O)NC1=O)C2=O]

4. The compound of claim 1, or a pharmaceutically acceptable salt thereof, wherein L is $C_{4-8}$ alkylene.

5. The compound of claim 1, or a pharmaceutically acceptable salt thereof, wherein L is $C_{4-9}$ heteroalkylene.

6. The compound of claim 1, wherein the compound has the formula:

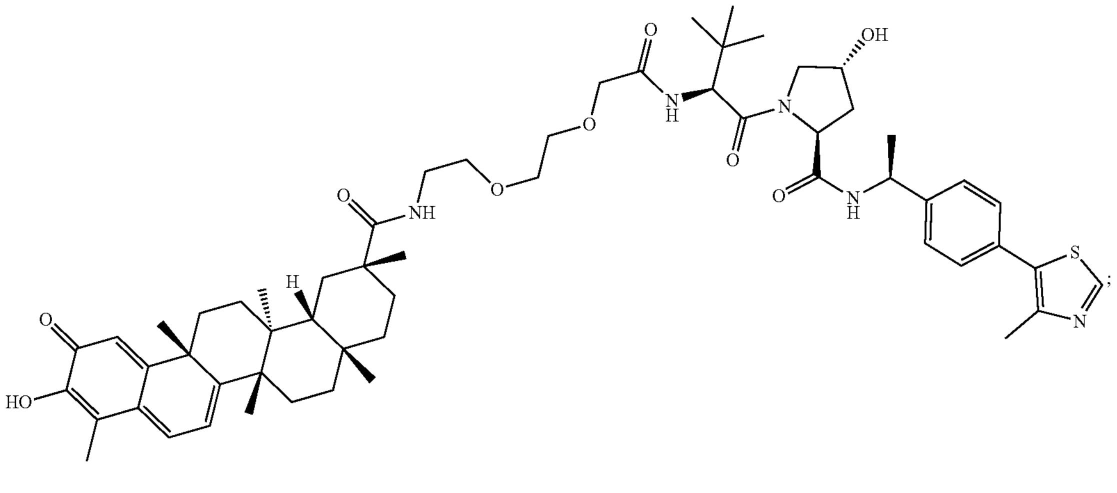

-continued
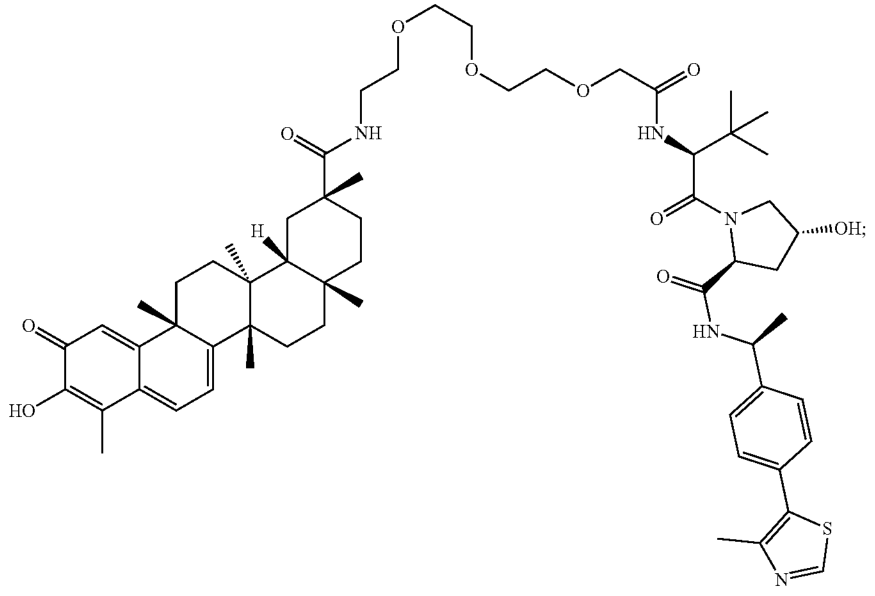
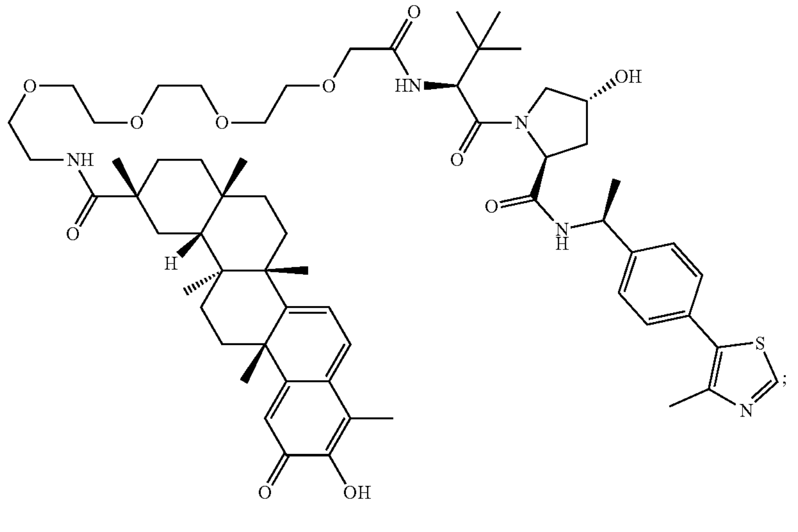
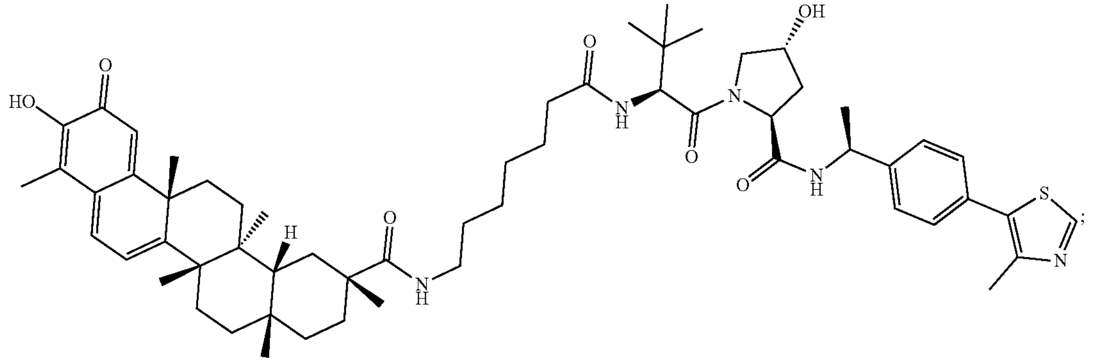

-continued
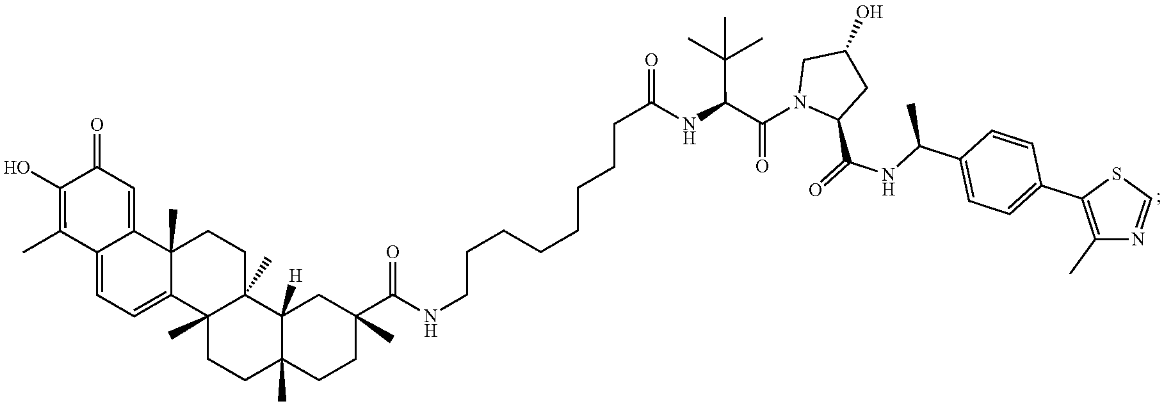
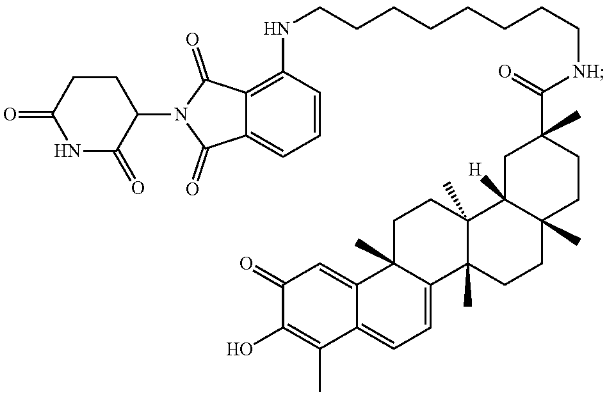
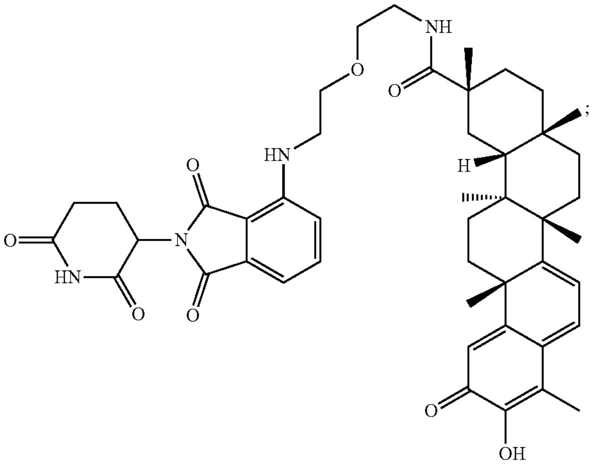
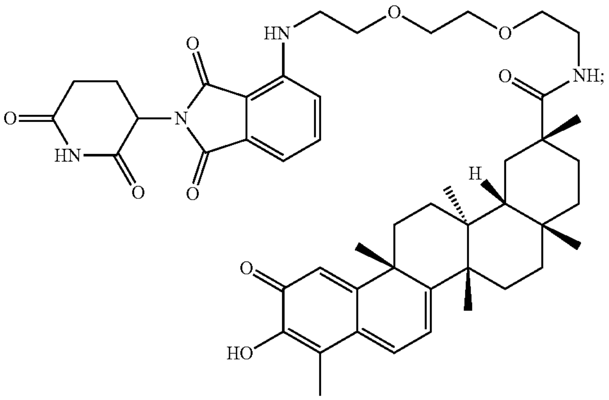
or

-continued

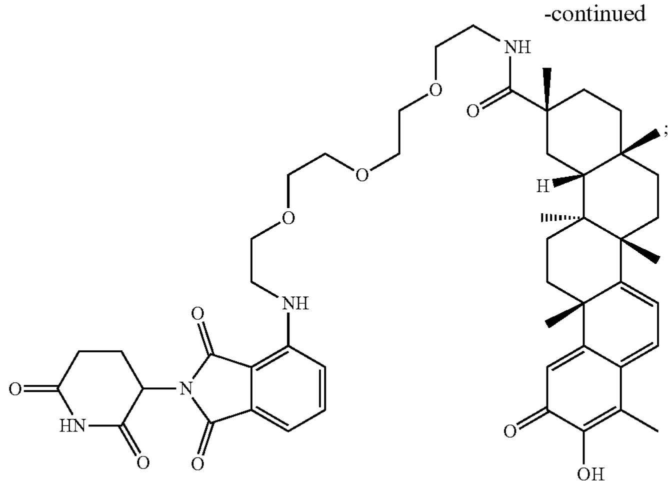

or a pharmaceutically acceptable salt thereof.

7. The compound of claim 6, wherein the compound is of the formula:

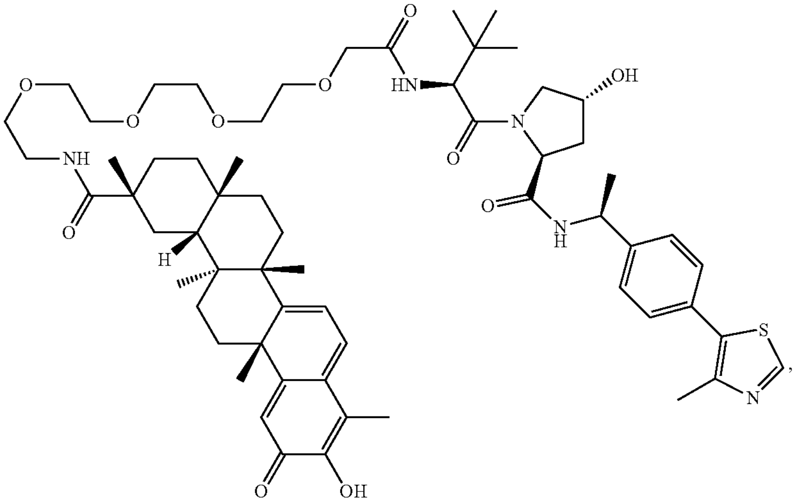 [SMILES: CC1=C(O)C(=O)C=C2C1=CC=C1[C@@]2(C)CC[C@@]2(C)[C@@H]3C[C@](C)(C(=O)NCCOCCOCCOCCOCC(=O)N[C@H](C(=O)N4C[C@H](O)C[C@H]4C(=O)N[C@@H](C)c4ccc(-c5scnc5C)cc4)C(C)(C)C)CC[C@]3(C)CC[C@]12C]

or a pharmaceutically acceptable salt thereof.

8. The compound of claim 6, wherein the compound is of the formula:

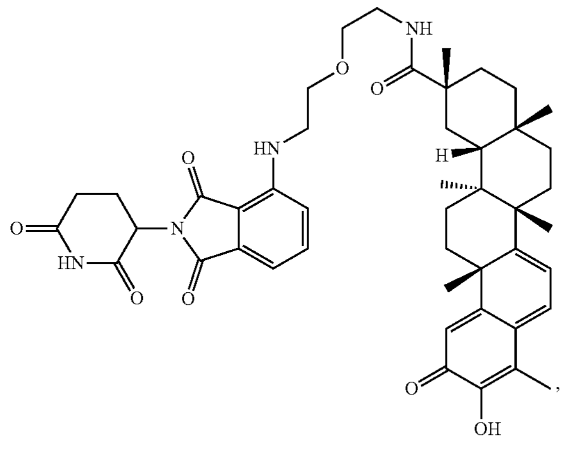 [SMILES: CC1=C(O)C(=O)C=C2C1=CC=C1[C@@]2(C)CC[C@@]2(C)[C@@H]3C[C@](C)(C(=O)NCCOCCNc4cccc5c4C(=O)N(C4CCC(=O)NC4=O)C5=O)CC[C@]3(C)CC[C@]12C]

or a pharmaceutically acceptable salt thereof.

9. The compound of claim 1, or a pharmaceutically acceptable salt thereof, wherein L is straight-chained $C_{4-8}$ alkylene.

10. The compound of claim 1, or a pharmaceutically acceptable salt thereof, wherein L is straight-chained $C_{4-9}$ heteroalkylene.

11. A pharmaceutical composition comprising an effective amount of a compound of claim 1, or a pharmaceutically acceptable salt thereof, a pharmaceutically acceptable carrier, and a pharmaceutically acceptable adjuvant.

12. The pharmaceutical composition of claim 11, further comprising an additional anti-cancer agent.

13. A method of treating cancer in a subject in need thereof, comprising administration of a compound of claim 1, or a pharmaceutically acceptable salt thereof, to the subject in need thereof, wherein the cancer is breast cancer, colon cancer, melanoma, renal cell cancer, endometrial cancer, or lung cancer.

14. The method of claim 13, wherein the cancer is colon cancer.

15. The method of claim 13, wherein the cancer is breast cancer.

16. The method of claim 13, further comprising administration of an additional anti-cancer agent to the subject in need thereof.

17. The method of claim 13, wherein the cancer is melanoma.

18. The method of claim 13, wherein the cancer is renal cell cancer, endometrial cancer, or lung cancer.

19. The method of claim 13, wherein the subject is a human.

* * * * *